(12) United States Patent
Wilson et al.

(10) Patent No.: US 7,799,560 B2
(45) Date of Patent: Sep. 21, 2010

(54) COMPARTMENTALIZED DEVICE FOR CELL CULTURE, CELL PROCESSING, AND SAMPLE DIALYSIS

(75) Inventors: John R. Wilson, New Brighton, MN (US); Daniel P. Welch, New Brighton, MN (US); Alison Robeck, New Brighton, MN (US); Douglas A. Page, New Brighton, MN (US)

(73) Assignee: Wilson Wolf Manufacturing Corporation, New Brighton, MN (US)

( * ) Notice: Subject to any disclaimer, the term of this patent is extended or adjusted under 35 U.S.C. 154(b) by 0 days.

(21) Appl. No.: 10/985,339

(22) Filed: Nov. 10, 2004

(65) Prior Publication Data

US 2005/0101009 A1 May 12, 2005

Related U.S. Application Data

(60) Provisional application No. 60/519,676, filed on Nov. 10, 2003.

(51) Int. Cl.
*C12M 3/06* (2006.01)
*C12M 1/12* (2006.01)
*C12N 5/00* (2006.01)

(52) U.S. Cl. ............... 435/297.1; 435/297.5; 435/298.2; 435/304.2; 435/401; 422/101; 210/321.63; 210/321.87

(58) Field of Classification Search ............... 435/297.1, 435/297.4, 297.5, 298.2, 304.2, 401; 422/101; 210/321.68, 321.87
See application file for complete search history.

(56) References Cited

U.S. PATENT DOCUMENTS 3,459,176 A * 8/1969 Leonard ............... 600/573
3,941,661 A  3/1976 Noteboom
4,296,205 A * 10/1981 Verma ................. 435/401

(Continued)

FOREIGN PATENT DOCUMENTS

CA 2105419 A * 3/1994

(Continued)

OTHER PUBLICATIONS

Mathiot et al. 'Increase of hybridoma productivity using an original dialysis culture system.' Cytotechnology. vol. 11 (1993), pp. 41-48.*

(Continued)

*Primary Examiner*—William H Beisner
(74) *Attorney, Agent, or Firm*—Patterson Thuente Christensen Pedersen, P.A.

(57) ABSTRACT

A versatile compartmentalized cell culture device, with a selectively permeable membrane separating the compartments, provides many attributes relative to traditional devices. It can be configured for high-density cell culture, co-culture, and sample dialysis while rolling or standing still. It can also be configured for continuous movement of liquid between compartments. The wide combination of attributes not found in other membrane based cell culture and bioprocessing devices includes more cell capacity, more cell secreted product capacity, higher cell and product density, increased medium capacity, minimized use of exogenous growth factors, compatibility with standard cell culture equipment and protocols, increased scale up efficiency, capacity to function when rolling or standing still, capacity for perfusion without the need for pumps, and more efficient sample dialysis.

17 Claims, 16 Drawing Sheets

U.S. PATENT DOCUMENTS

| | | | | |
|---|---|---|---|---|
| 4,317,886 A | | 3/1982 | Johnson et al. | |
| 4,748,124 A | | 5/1988 | Vogler | |
| 4,824,787 A | | 4/1989 | Serkes et al. | |
| 4,829,004 A | | 5/1989 | Varani et al. | |
| 4,912,058 A | | 3/1990 | Mussi et al. | |
| 5,324,428 A | | 6/1994 | Flaherty | |
| 5,426,037 A | * | 6/1995 | Pannell et al. | 435/70.21 |
| 5,449,617 A | | 9/1995 | Falkenberg et al. | |
| 5,503,741 A | | 4/1996 | Clark | |
| 5,527,705 A | | 6/1996 | Mussi et al. | |
| 5,576,211 A | | 11/1996 | Falkenberg et al. | |
| 5,686,301 A | | 11/1997 | Falkenberg et al. | |
| 5,693,537 A | | 12/1997 | Wilson et al. | |
| 5,702,945 A | | 12/1997 | Nagels et al. | |
| 5,783,075 A | | 7/1998 | Eddleman et al. | |
| 5,866,400 A | | 2/1999 | Palsson et al. | |
| 5,866,419 A | | 2/1999 | Meder | |
| 6,130,080 A | | 10/2000 | Fuller | |
| 6,150,159 A | * | 11/2000 | Fry | 435/304.1 |
| 6,468,792 B1 | | 10/2002 | Bader | |
| 6,605,463 B1 | * | 8/2003 | Bader | 435/298.2 |
| 2003/0077816 A1 | | 4/2003 | Kronenthal et al. | |

FOREIGN PATENT DOCUMENTS

| | | |
|---|---|---|
| DE | 4229334 A1 * | 3/1994 |
| EP | 0 700 990 A2 | 3/1996 |
| FR | 2 666 094 | 2/1992 |

OTHER PUBLICATIONS

BabbleFish translation of FR2666094 (Feb. 28, 1992).*

* cited by examiner

FIG. 7B   DETAIL A

COMPARTMENTALIZED DEVICE FOR CELL CULTURE, CELL PROCESSING, AND SAMPLE DIALYSIS

RELATED APPLICATION

The present application claims priority to U.S. Provisional Application No. 60/519,676 filed Nov. 10, 2003, which is hereby incorporated herein in its entirety by reference.

GOVERNMENT INTERESTS

This invention was made in part with U.S. Government support under National Institutes of Health Small Business Innovative Research Grant 2 R44 HL065977-02 "Membrane Based Roller Bottle". The U.S. Government may have certain rights in this invention.

TECHNICAL FIELD

This invention relates to devices and methods for growing cells, processing cells, and dialyzing samples.

DISCUSSION OF LIMITATIONS OF CONVENTIONAL TECHNOLOGIES DESCRIBED IN RELATED ART

Devices integrating semi-permeable membranes have a variety of uses in the cell culture field. Their uses include high-density cell culture, co-culture, cell infection, and sample dialysis. However, existing devices have deficiencies that limit their efficiency and usefulness.

Static membrane-based devices for high-density cell culture have been proposed and commercialized. The CEL-Line™ products from Integra Biosciences, related to U.S. Pat. No. 5,693,537 (Wilson et al.), are commercialized devices are in the form of a flask, separated into two compartments by way of a 10,000 molecular weight cutoff (MWCO) semi-permeable dialysis membrane. They are advantageous for small-scale production because they are easy to use. However, these devices have scale up inefficiencies because they utilize a dialysis membrane in sheet form. To increase the number of cells present, the dialysis membrane must increase in surface area. Since the membrane is in sheet form, the footprint of the device must get proportionally larger. Devices with large footprints use incubator space inefficiently. Furthermore, as dialysis membranes get larger in surface area, the probability of rupture increases. Another deficiency is the limited height at which medium resides in the devices, requiring an increase in device footprint as more medium is required to feed the increased quantity of cells residing in the devices. U.S. Pat. No. 4,748,124 (Vogler) and U.S. Pat. No. 6,468,792 (Bader) also introduce compartmentalized gas permeable devices. Vogler '124 discloses a dialysis membrane for compartmentalization, while Bader '792 relies upon a microporous membrane. Unfortunately, they suffer the same scale up limitations as the CELLine™ products.

Attempts have been made to improve the roller bottle by compartmentalizing the device with a semi-permeable membrane. However, each attempt has deficiencies, and little commercial impact in the market has been achieved. Deficiencies include the requirement of non-standard roller mechanisms, inability to interface with pipettes, incompatibility with common materials for adherent culture, and scale up limitations due to the limited amount of medium that can reside in the devices.

U.S. Pat. Nos. 5,449,617 and 5,576,211 (Falkenberg et al.) describe a gas permeable roller bottle compartmentalized by a dialysis membrane. By separating the cells and cell-secreted products from the nutrient medium by way of the dialysis membrane, it is capable of increasing cell and cell-secreted product density. The maximum medium volume that can be accommodated by the bottle is 360 ml, of which 60 ml resides in the cell compartment and 300 ml in the nutrient compartment. Its scale up potential is limited by the 360 ml medium capacity, which leads to an excessive number of devices for scale up. Also, it is not suitable for adherent culture because it makes no provision for attachment surface area. Furthermore, the dialysis membrane can only increase in surface area as the bottle diameter increases, since it is perpendicular to the bottle axis of rotation. This restricts mass transfer.

U.S. Pat. No. 5,686,301 (Falkenberg et al.) describes an improved version of the devices defined in U.S. Pat. Nos. 5,449,617 and 5,576,211. A feature in the form of collapsible sheathing that prevents damage by internal pressurization is disclosed. However, no improvement in the volume of medium that can reside in the device is made. Also, the limited dialysis membrane surface area is not addressed. Furthermore, it remains unsuitable for adherent culture.

Vivascience Sartorius Group sells a product called the MiniPERM that is related to the Falkenberg et al. patents. The maximum cell compartment module is 50 ml and the maximum nutrient module is 400 ml. Thus, the maximum volume of medium that can reside in the commercial device is only 450 ml. The small size of the commercial device, the need for custom rolling equipment, the inability to be used with traditional laboratory pipettes, the potential for cell shear, the inability to allow microscopic viewing of cells, and the lack of suitability for adherent culture limits its value as an alternative to the traditional bottle.

The device disclosed in U.S. Pat. No. 5,702,945 (Nagels et al.) attempts to improve the MiniPERM device by improving its capacity to culture adherent cells. One cell attachment matrix is provided in the cell culture compartment at the inner face of the gas permeable membrane. Although adherent culture is possible, it only offers a small surface for adherent cells relative to the traditional bottle. Also, microscopic assessment of cell confluence and morphology is not accommodated.

Co-culture applications are typically conducted in small devices like the Transwell® device from Corning. These devices are for very small-scale culture only. U.S. Pat. No. 5,527,705 (Mussi et al.) attempts to provide a large scale co-culture alternative by use of a compartmentalized roller bottle. The bottle is compartmentalized by way of two coaxial cylindrical containers of similar length, the inner container being centered within the exterior receptacle. A microporous membrane physically separates the cell population residing within the inner container from the cell population residing in the exterior receptacle. There is no discussion or guidance for how to prevent the inner container from causing disturbances in the inoculum residing in the exterior receptacle. On the contrary, a recommended distance D between containers of 0.010 inches to about 0.040 inches dictates that the microporous membrane will move through liquid residing in the exterior receptacle. Because the recommended inoculation volume of a traditional roller bottle is 170 to 255 ml, but contact with the microporous membrane occurs at about 15 ml to 80 ml depending on the distance D, disturbance of the inoculum by the microporous membrane is virtually assured. Unfortunately, cells have a difficult time seeding normally when there are disturbances to the medium in which they reside because their specific gravity is typically nearly that of the medium. Thus, disturbance to the inoculum as the compartmentalized roller bottle rotates can prevent cells from properly gravitating to the inside surface of the exterior receptacle. Support members, preferably extending from a first end to a second end of the inner container are used to physically create the distance D, and will further disturb the inoculum. Thus, although the roller bottle for co-culture attempts to provide a good alternative to the Transwell® device, its geometry interferes with a normal inoculation process.

The use of devices, compartmentalized by a microporous membrane, for increasing the frequency of contact between vectors and stationary target cells has been described by U.S. Pat. No. 5,866,400 (Palsson et al.). This approach relies on a microporous membrane of 0.1 microns to about 2.0 microns to retain cells in one compartment, while vectors move past the trapped cells and through the microporous membrane. This increases the amount of contact between vectors and cells relative to methods that rely on Brownian motion and improved infectivity rates. To further increase the rate of infectivity, vectors can be recycled back into the compartment containing cells by the use of a pump. Unfortunately, the use of pumps adds complexity to the process.

Devices that rely upon dialysis membrane are commonly used to alter the molecular composition of samples residing in them. Placing the sample in a container that is comprised of a dialysis membrane, and immersing the container in a second container holding a dialysate solution allows control over the final composition of the solution. Two styles of products dominate the market. The first style consists of dialysis tubing, such as that marketed by Spectrum Labs and described in U.S. Pat. No. 5,324,428 (Flaherty) and U.S. Pat. No. 5,783,075 (Eddleman et al.). Disadvantageous membrane surface area to sample volume ratio are inherent. The second style is a cartridge format marketed by Pierce Chemical under the trade name Slide-A-Lyzer® (U.S. Pat. No. 5,503,741—Clark). It requires the use of a syringe and needle, which is not a preferred liquid handling method compared to pipettes. It is also limited in size, about a 10 ml sample volume, because it requires the membrane to be flat. Thus, it quickly outgrows typical dialysate containers. Furthermore, unsupported sheet membranes are more likely to break as they get larger and larger.

In summary, a variety of devices compartmentalized by various semi-permeable membranes are used in high-density cell culture, co-culture, cell processing, and sample dialysis applications. However, these membrane-based devices have inherent deficiencies that limit their efficiency and usefulness. Membrane based devices that seek to create high-density cell culture do not provide geometry that is suitable for efficient scale up. The attempt to provide scaled up co-culture in a membrane based roller bottle fails to allow cells to gravitate in the same manner as the Transwell® device or the traditional roller bottle. The use of membrane-based flow through devices to increase the rate of infectivity is complicated by the need for pumps when vectors are recycled. For sample dialysis, dialysis tubing provides a poor surface area to sample volume ratio, and Slide-A-Lyzer® dialysis cartridges require the use of needles. Improved devices that overcome these deficiencies are needed.

SUMMARY OF THE INVENTION

It is an object of the present invention to disclose multiple formats for a device compartmentalized by a semi-permeable membrane, that are superior to previous compartmentalized cell culture, co-culture, cell processing, and laboratory sample dialysis devices. This compartmentalized device can be configured to allow high-density cell culture while rolling or standing still, to allow co-culture without disruption of inoculum, to physically move liquid from one compartment to the other, and to perform more efficient dialysis of laboratory samples.

According to one embodiment of the invention, a basal medium compartment and a cell culture compartment are separated by a semi-permeable membrane to create an improved high-density cell culture device. It can be configured to improve upon prior high-density roller bottles in many ways that include holding more medium, allowing the use of pipettes, letting adherent cells attach just as they do in traditional roller bottles, allowing microscopic viewing just as is done in traditional roller bottles, and functioning on standard roller racks. The benefits of the novel compartmentalized device include the ability to increase the concentration of cells and cell-secreted products, allow a longer duration of time between feeding periods, minimize the amount of wasted space inherent to traditional roller bottles, without losing the desired features inherent to the traditional bottle such as ease of use, microscopic evaluation, pipette access, and compatibility with standard roller racks. This embodiment can also be configured to more efficiently dialyze laboratory samples than currently used laboratory dialysis tubing or cartridges.

According to another embodiment of the invention, an improved large-scale co-culture device is created. It improves upon prior art by creating geometric relationships between the basal medium compartment and the cell culture compartment that retain the desired attributes of a traditional roller bottle, such as uniform cell seeding, microscopic evaluation, pipette access, and compatibility with standard roller racks.

According to another embodiment of the present invention, an improved compartmentalized device is created that is capable of functioning when rolling or standing. Advantages of this novel compartmentalized cell culture device include the ability to function when rolled or unrolled. When in the unrolled position, it improves upon prior unrolled compartmentalized devices by allowing configurations that include a higher semi-permeable membrane surface area to medium volume, more medium height, and improved scale up efficiency.

According to another embodiment of the present invention, liquid is continuously moved from one compartment to the other while the device rolls. A suspended compartment is fabricated in part with a semi-permeable membrane, capable of passing liquid. The suspended compartment remains stationary as a surrounding compartment rotates about it. A physical feature collects medium from the surrounding compartment, and deposits it to the suspended compartment by the rolling action of the bottle. Medium is returned to the surrounding compartment by passing through the semi-permeable membrane.

According to another embodiment of the present invention, a suspended compartment resides in the device. The device is rolled and configured to impart motion to the suspended compartment to simulate the action of a shaker plate.

BRIEF DESCRIPTION OF THE DRAWINGS

FIGS. 7A and 7B show one configuration for mating a cylindrically shaped semi-permeable membrane to the basal medium compartment in a liquid tight manner.

DETAILED DESCRIPTION OF THE INVENTION

Figure 1A:
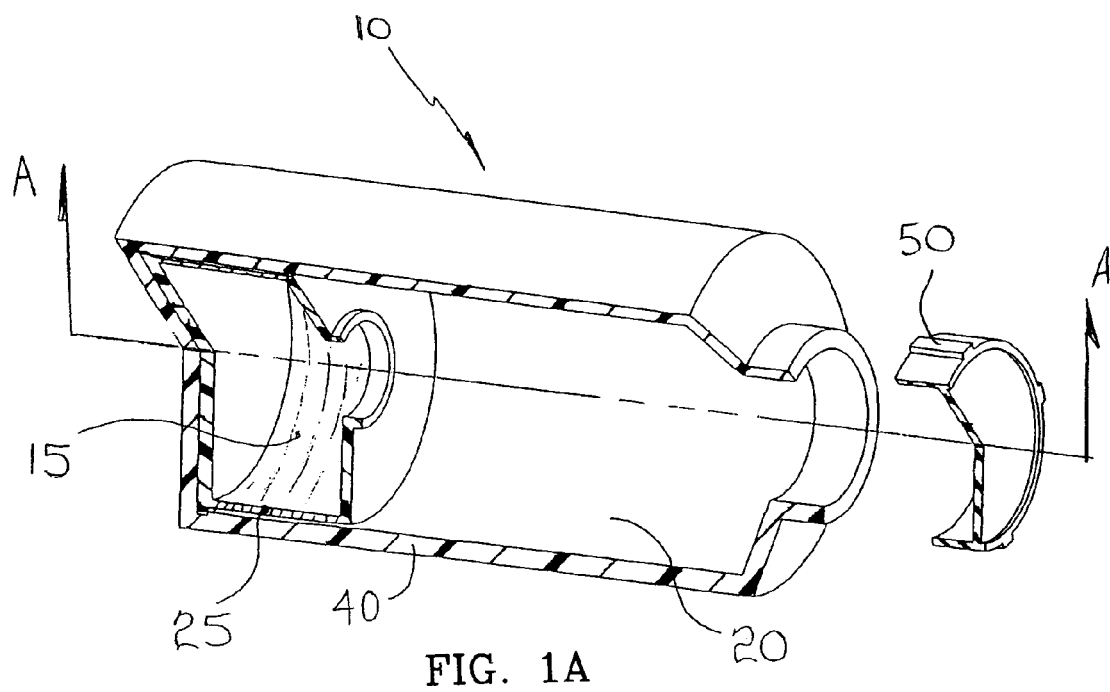
FIGS. 1A and 1B show a compartmentalized device, configured to culture cells when rolling in a manner similar to a roller bottle.
Figure 1B:
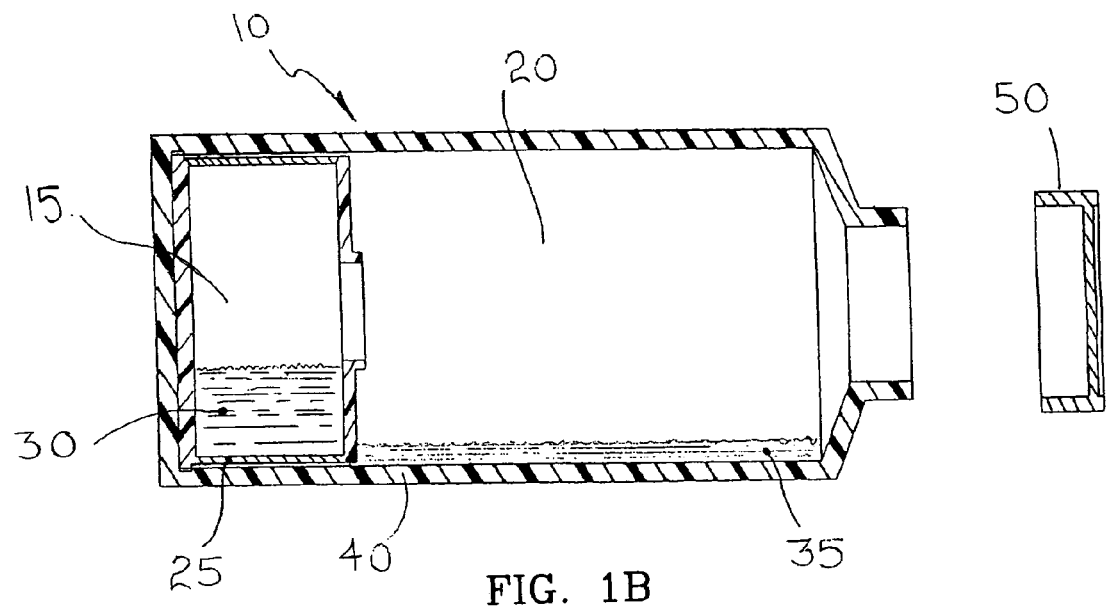

FIG. 1A shows a cutaway of compartmentalized device 10, configured to culture cells when rolling in a manner similar to a traditional roller bottle. A basal medium compartment 15 resides within compartmentalized bottle 10. Cell culture compartment 20 is separated from basal medium compartment 15 by semi-permeable membrane 25. Cap 50 protects compartmentalized device 10 from contaminants. FIG. 1B shows cross-section A-A of FIG. 1A. Semi-permeable membrane 25 forms a portion of basal medium compartment 15. Basal medium 30 resides within basal medium compartment 15, and cell culture medium 35 resides in cell culture compartment 20. Communication between basal medium 30 and cell culture medium 35 occurs by way of semi-permeable membrane 25. By configuring compartmentalized device 10 in this manner, it can be used to concentrate cells and cell secreted products in cell culture compartment 20 because cells and cell-secreted products can be retained in cell culture compartment 20 when medium is exchanged in basal medium compartment 15. Compartmentalized device 10 can also be used for co-culture, when cells are cultured in culture compartment 20, and cells are cultured in basal medium compartment 15.

The characteristics of semi-permeable membrane 25 determine what is allowed to pass between basal medium 30 and cell culture medium 35, and what is retained in cell culture compartment 20. Many sources of information are available that describe what characteristics of semi-permeable membrane 25 are desirable for a particular cell culture application. For example, the CELLine™ products rely upon a 10,000 MWCO regenerated cellulose acetate membrane, which has proved very effective in high-density monoclonal antibody production. In cases where co-culture is desired, the semi-permeable membrane can act to separate the cells from physical contact, but allow secreted products to travel back and forth across the semi-permeable membrane. Microporous membranes are typically used for co-culture applications. Sources of information that can be used to provide guidance in the selection of an appropriate semi-permeable membrane include Wilson et al. '537, Vogler '124, Bader '792, Mussi et al. '705, Millipore (Billerica, Mass.), Spectrum Laboratories Inc. (Rancho Dominguez, Calif.), and Biovest International (Coon Rapids, Minn.).

Device housing 40 can be any biocompatible material. In the preferred embodiment, it is rigid and optically clear. Polystyrene is a common material used for flasks and roller bottles. If the device housing is made of polystyrene, it can exhibit the same attachment characteristics of traditional devices. This can be helpful when scientists are scaling a culture out of traditional flasks and roller bottles into the compartmentalized device. In the preferred embodiment, the device housing is cylindrical to facilitate rolling. However, other shapes are possible. For example, the shape described in U.S. Pat. No. 5,866,419 (Meder) can easily be integrated into the design. Those skilled in the art will recognize that shapes for the device housing that are not cylindrical can be adapted for a roller rack by attaching a cylindrical housing to the non cylindrical device housing. Preferably, basal medium compartment conforms to the shape of the device housing so that the distance from the semi-permeable membrane to the device housing is uniform about its perimeter.

Figure 2A:
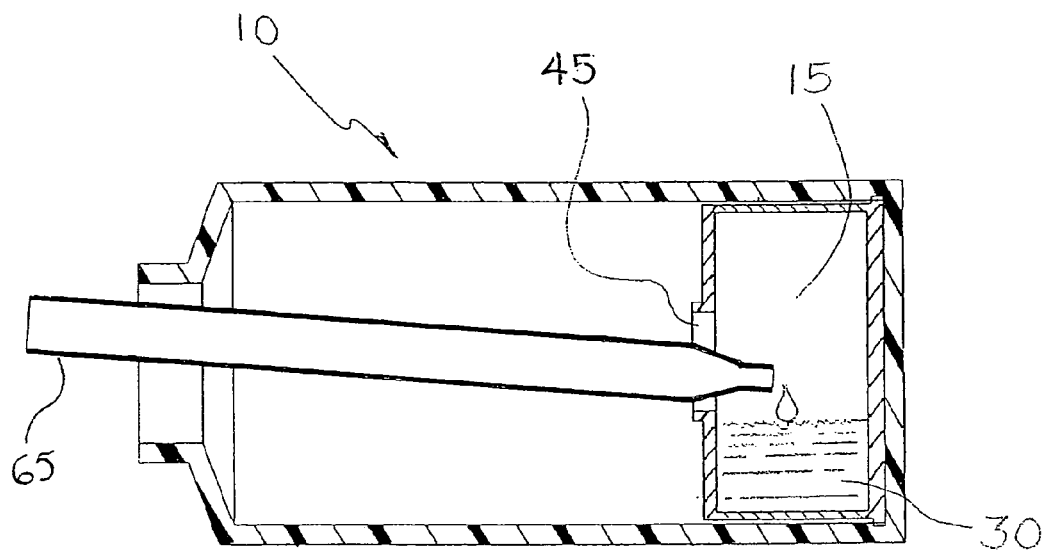
FIGS. 2A and 2B show how medium and cell culture medium can be introduced into the compartmentalized device with pipettes.
Figure 2B:
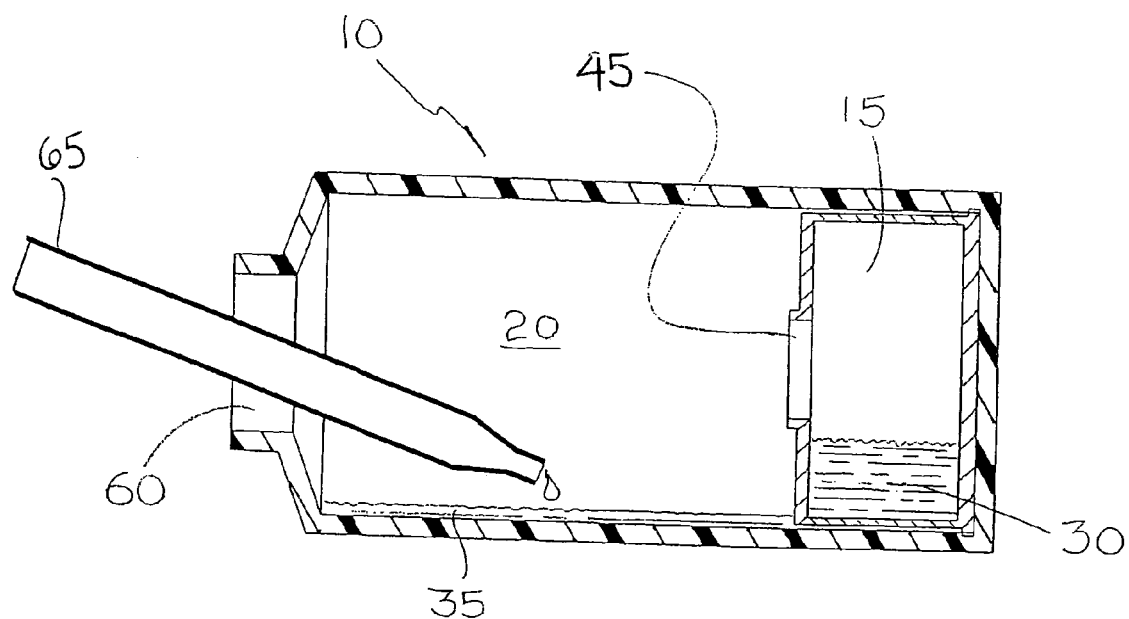

Those skilled in the art will recognize there are many ways to structure the compartmentalized device as a closed system by way of septums, sterile tubing connections, and the like. However, accommodating the use of a pipette is advantageous when a there is a desire to retain the simplicity of traditional devices. FIGS. 2A and 2B show how medium and cell culture medium can be introduced into the compartmentalized device with pipettes. In FIG. 2A, pipette 65 is used to dispense basal medium 30 into basal medium compartment 15 by way of basal medium compartment access port 45. In FIG. 2B, pipette 65 is used to dispense cells and cell culture medium 35 into cell culture compartment 20 by way of cell culture compartment access port 60.

The basal medium compartment has the role of holding enough basal medium to provide an appropriate source of substrates and an appropriate sink for waste products. Thus, a primary design consideration is the amount of medium required for a given cell culture application. Increasing the volume of the basal medium can reduce feeding frequency relative to traditional devices. For example, if 300 ml of basal medium residing in a traditional roller bottle supports 300× $10^6$ cells and needs to be exchanged every day, putting 600 ml of basal medium in the basal medium compartment can reduce the feeding schedule to every two days. Placing the cells and a small volume of cell culture medium in the cell culture compartment, and placing a relatively large volume of medium in the basal medium compartment can increase cell density. For example, if $300 \times 10^6$ cells typically reside in 300 ml of medium in a traditional roller bottle, placing cells and 10 ml of cell culture medium in the cell culture compartment, and 300 ml of basal medium in the basal medium compartment will increase cell density by about 30-fold without a change in the feeding schedule.

One design consideration for the basal medium compartment is related to hydrostatic pressure differential across the semi-permeable membrane. When the height of basal medium exceeds the height of cell culture medium, as shown for example in FIG. 1B, hydrostatic pressure differential across the membrane will be created. Thus, liquid from the basal medium compartment will tend to move into the cell culture compartment. Care should be taken to ensure that liquid moving into the cell culture compartment does not dilute important substances that may reside in the cell culture medium, such as serum. This effect can be controlled by proper selection of the semi-permeable membrane. Factors to consider include MWCO, material, surface area, and membrane thickness. Typically, microporous semi-permeable membranes will allow liquid to move through them much more quickly than ultrafiltrative semi-permeable membranes at a given hydrostatic pressure differential. Liquid flux is also proportional to surface area. The liquid flux characteristic should be evaluated on a case by case basis when properly designing the compartmentalized device. For example, we have determined that 10,000 MWCO regenerated cellulose membranes from AKZO Nobel, with a 3 $cm^2$ surface area, allowed almost no liquid to move across it over a 5-day period when the basal medium resided at a height of 2.0 inches above the semi-permeable membrane. On the other hand, we have also determined that 0.4 micron microporous membranes from Nucleopore®, with a 3 $cm^2$ surface area, allowed a 1.75 inch drop in liquid height over a 5-day period when the basal medium initially resided at a height of 2.0 inches above the semi-permeable membrane.

The height of basal medium can be controlled by the geometry of the basal medium compartment. For a given volume of medium, simply structuring the basal medium compartment to increase in length will reduce the height of the medium. Thus, hydrostatic pressure differential can be reduced by the geometry of the basal medium compartment.

Movement of liquid across the semi-permeable membrane can also occur when the protein concentration of the cell culture medium is increased relative to the basal medium, as may be the case when cells and cell-secreted products reside at high-density. High osmolarity of the cell culture medium will then draw liquid from the basal medium across the semi-permeable membrane. This is not uncommon with commercial devices that are compartmentalized by way of a dialysis membrane. Protocols can be adjusted to minimize any detrimental effect on the culture. For example, in applications where serum resides in the cell culture medium, but not in the basal medium, the CELLine™ product literature suggests increasing the concentration of serum by about 5% over that used in traditional devices. In this manner, the dilution of serum by liquid transfer across the dialysis membrane will not bring the concentration below that which the cells experienced as they were scaled up from cryopreservation.

Preferably, the basal medium compartment is structured in a manner that makes the most effective use of the semi-permeable membrane. That can be achieved by configuring the basal medium compartment to rotate as the compartmentalized device rotates. Doing so allows the semi-permeable membrane to become wetted across its entire surface area, and can increase mass transfer between the basal medium and the cell culture medium. In the case of co-culture, where cells may be attached to the semi-permeable membrane, doing so increases the surface area for cells to reside upon and allows attached cells to experience gas exchange in a similar manner as the traditional roller bottle.

Many design approaches are possible to ensure the basal medium compartment rotates as the compartmentalized device rotates, as those skilled in the art will recognize. The basal medium compartment can rotate in the same direction of the device housing, or in the opposite direction. For example, physically connecting the basal medium compartment to the device housing allows it to rotate in the same direction. The physical connecting points should be selected, and configured, to prevent interference with the withdrawal of liquid from the cell culture compartment. Allowing the basal medium compartment to rotate in the opposite direction of the device housing can be achieved by a variety of methods, as those skilled in the art will recognize. In this case, a cylindrically shaped basal medium compartment and device housing are preferred. Whether or not the basal medium compartment is physically attached to the device housing, opposite rotation can be attained just from the frictional force between the basal medium compartment and the device housing. Modifying the surface finish at the contact points between the basal medium compartment and the device housing can alter friction. A geared interface between the basal medium compartment and the device housing is another way of achieving opposing rotation. Care should be taken that the interface does not prevent cell culture medium from moving freely about the length of the cell culture compartment. If opposing rotation is desired with the basal medium compartment physically connected to the bottle housing, any linkage that allows the basal medium compartment to rotate in the opposite direction of the device housing will suffice. For example, a frictionless rotary union is one option.

Figure 3A:
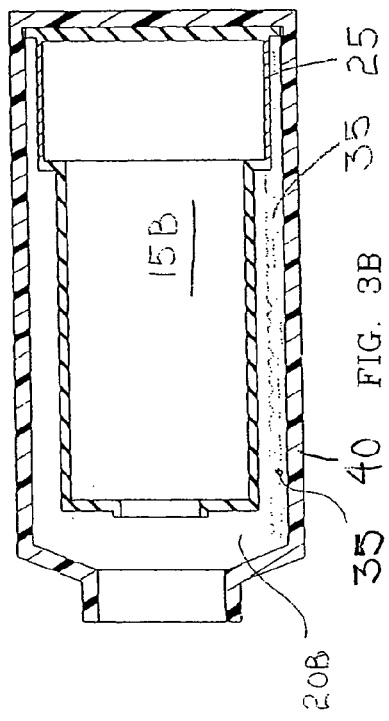
FIGS. 3A, 3B, 3C and 3D show examples of how the geometry of the basal medium compartment can be altered to minimize disturbances to the inoculum.
Figure 3C:
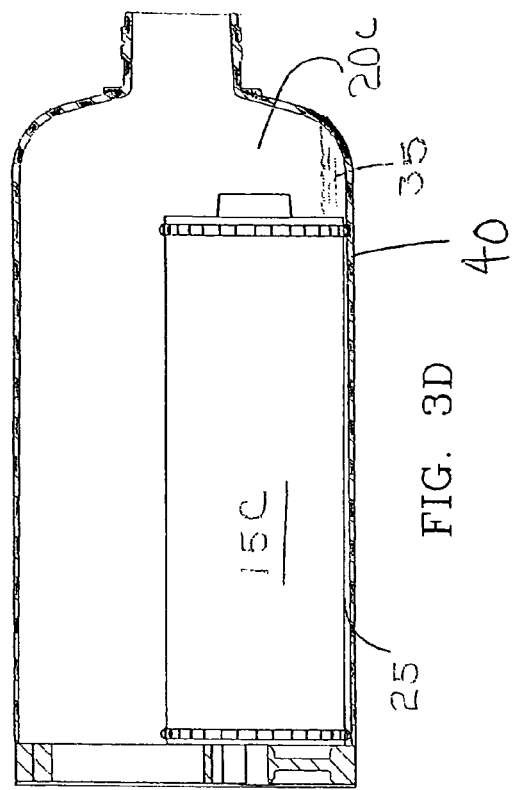
Figure 3B:
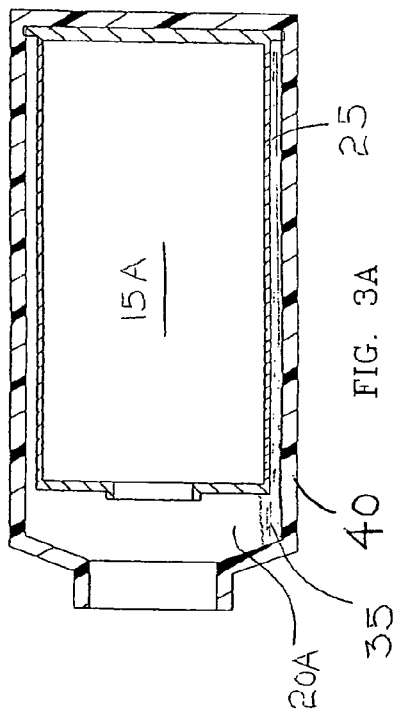

Another design consideration for the basal medium compartment is related to its physical contact with the cell culture medium in the cell culture compartment. Physical contact can cause perturbations in the cell culture medium and affect the manner in which adherent cells deposit onto the device housing, and can cause cell shear in suspension cell culture applications. Examples of alternative geometries, and the contact each makes with inoculum and cell culture medium, are shown in FIGS. 3A, 3B, and 3C. In FIG. 3A, basal medium compartment 15A extends throughout cell culture compartment 20A. In FIG. 3B, basal medium compartment 15B extends throughout cell culture compartment 20B, but its profile is designed to allow basal medium compartment 15B to avoid contact with cell culture medium 35 in areas other than where semi-permeable membrane 25 exists. In FIG. 3C, basal medium compartment 15C extends throughout cell culture compartment 20C, and is elevated a greater distance beyond the lower portion of device housing 40 than the configuration of FIG. 3A.

Inoculum makes contact with the basal medium compartment of each configuration in a different manner. In FIG. 3A, contact is made with cell culture medium 35 along the length of basal medium compartment 15A. In FIG. 3B, contact is made with cell culture medium 35 along a small portion of the length of basal medium compartment 15B, which is preferably comprised mainly of semi-permeable membrane 25. In FIG. 3C, no contact is made with cell culture medium 35 because basal medium compartment 15C remains elevated as bottle housing 40 rolls. When using the configuration of FIG.

Figure 3D:
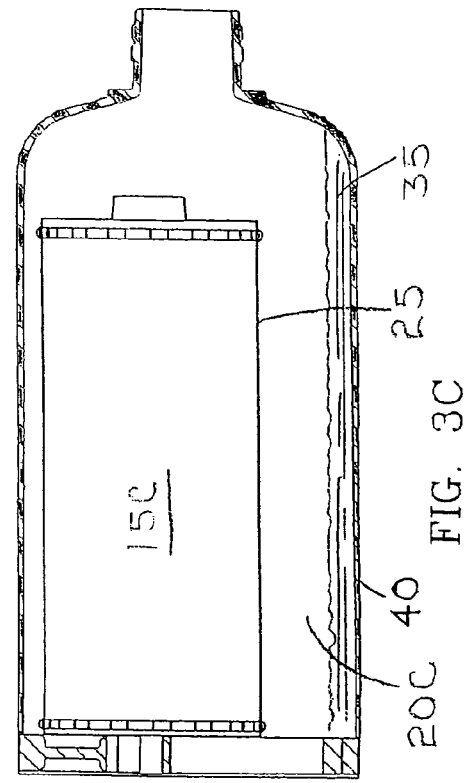

3C, after cells have seeded from cell culture medium 35, there are two options to place cell culture medium in communication with basal medium by way of semi-permeable membrane 25. The first option is by increasing the volume of cell culture medium 35 in cell culture compartment 20C until it makes contact with semi-permeable membrane 25. The second option is to lower basal medium compartment 15C post inoculation, as shown in FIG. 3D, to so that semi-permeable membrane 25 makes contact with cell culture medium 35. This second option allows a much smaller volume of cell culture medium to reside in cell culture compartment 20C than the first option. FIG. 3D shows basal medium compartment 15C repositioned to allow a small volume of cell culture medium 35 to reside in cell culture compartment 20C and to make contact with semi-permeable membrane 25.

Figure 4A:
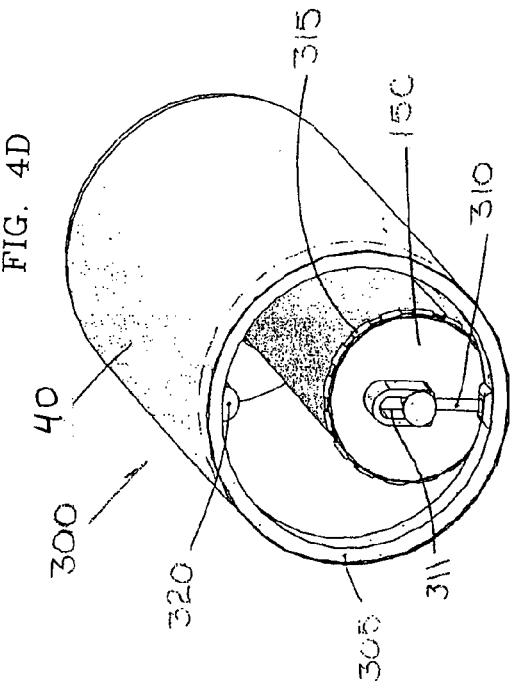
FIGS. 4A, 4B, 4C, and 4D show an example of how to move the basal medium compartment from an inoculation position to a feeding position.
Figure 4B:
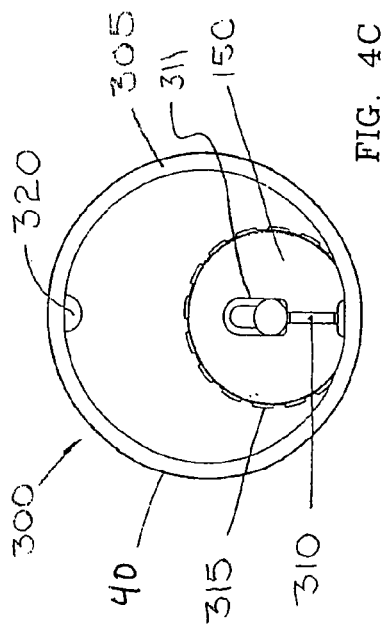
Figure 4D:
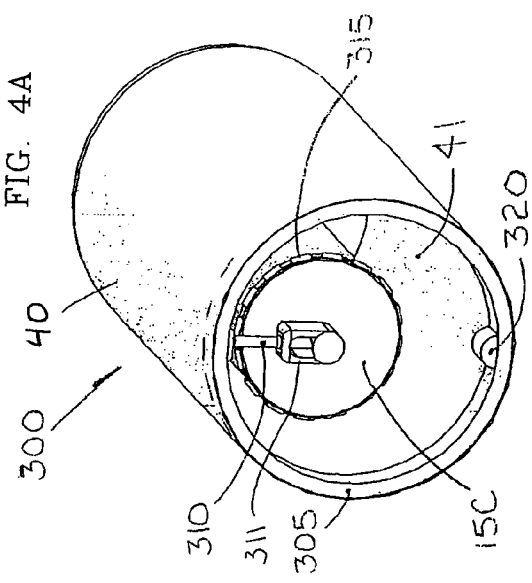
Figure 4C:
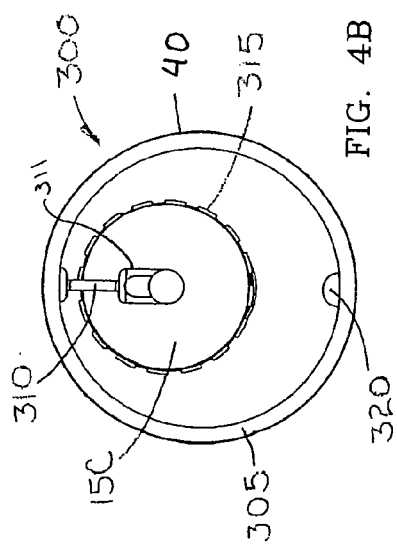

Moving basal medium compartment 15C into the lowered position can be achieved in any number of ways, as those skilled in the art of cell culture device design and mechanical engineering will recognized. A wide variety of mechanisms are possible. One technique is to use the weight of the basal medium to drive the basal medium compartment into the lowered position, as shown in FIG. 4A through FIG. 4D. The technique described allows the basal medium compartment to automatically move into a feeding position when medium is added to the basal medium compartment. FIGS. 4A and 4D show perspective views from the rear of compartmentalized device 300, which is configured with one way to achieve this objective. FIG. 4B shows a rear view of compartmentalized device 300 of FIG. 4A. FIG. 4C shows a rear view of compartmentalized device 300 of FIG. 4D. Basal medium compartment 15C is held in frictionless slot 311. Frictionless slot 311 is integral to connection rod 310, which mates to positioning ring 305. As best shown in FIG. 4B, basal medium compartment 15C is elevated so that it does not disturb inoculum or cell culture medium. Positioning ring 305 makes frictionless contact with device housing 40. Counter weight 320 is attached to positioning ring 305, and connected rod 310 is mounted to positioning ring 305 directly opposite counter weight 320. Counter weight 320 exceeds the weight of basal medium compartment 15C. Therefore counter weight 320 forces positioning ring 305 to rotate until counter weight 320 is at the lowest point, forcing connecting rod 310 and basal medium compartment 15C to reside directly above it. Gravity causes basal medium compartment 15C to fall to the lowest point allowed by slot 311. The dimensions of slot 311 can be altered to place basal medium compartment 15C at various desired heights relative to device housing 40. When cells need to be fed, adding basal medium to basal medium compartment 15C automatically places basal medium compartment 15C in contact with cell culture medium. When the weight of basal medium compartment 15C increased beyond that of counter weight 320, due to the added weight of the basal medium, any motion that moves basal medium compartment 15C off center will allow gravity to place it in the lowered position. That motion can come by moving basal medium compartment 15C slightly with a pipette, just from the simple act of carrying compartmentalized device 300 from the laminar flow hood to the incubator, or from the action of the roller mechanisms on device housing 40. Once basal medium compartment 15C gets off center, a lever arm is created and its weight overcomes counter weight 320, and frictionless positioning ring 305 rotates until basal medium compartment 15C comes to reside at the lowest point possible. Feet 315 make contact with device housing 40. By creating the appropriate amount of friction between feet 315 and device housing 40, basal medium compartment 15C can be made to roll in the opposite direction of device housing 40.

Figure 5A:
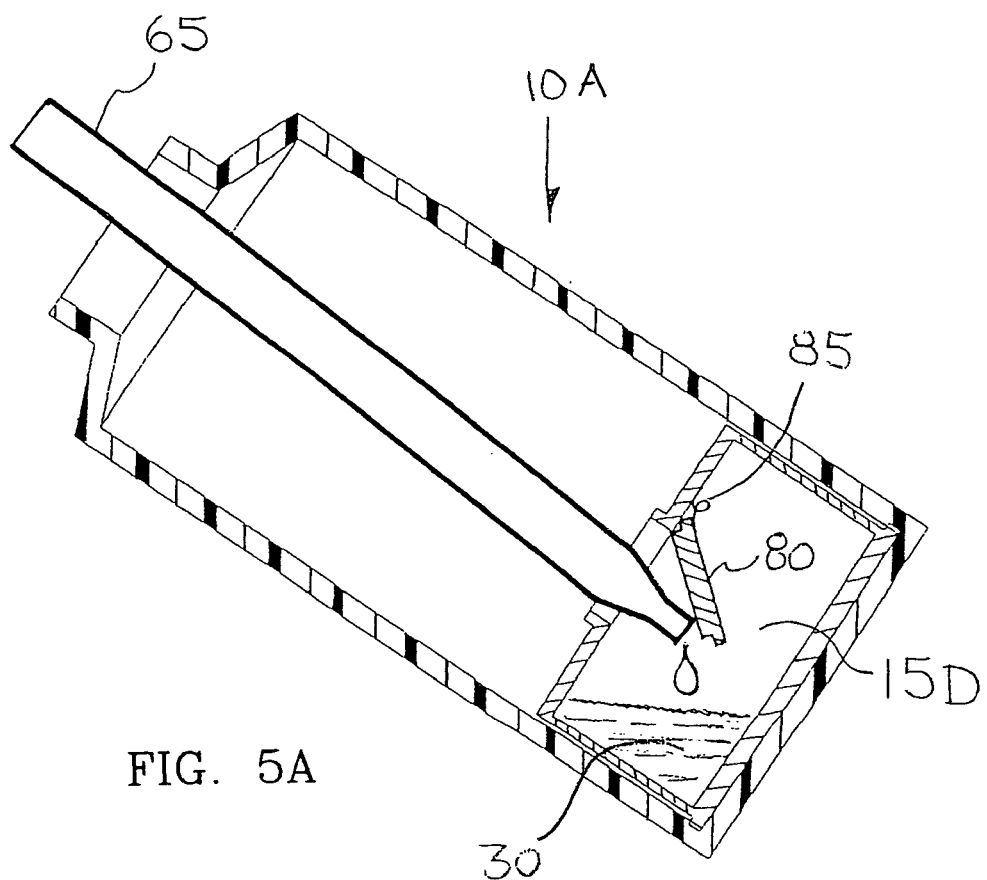
FIGS. 5A and 5B show one example of how to create a basal medium access port cover that can retain basal medium in the basal medium compartment.
Figure 5B:
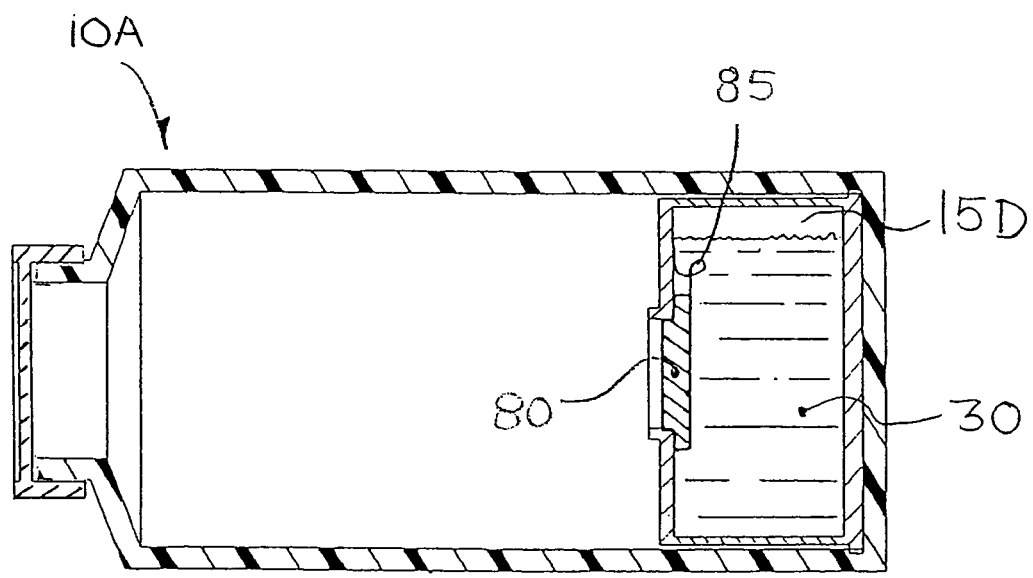

Structuring the basal medium compartment so that basal medium can reside within it can be achieved in a number of ways. If the height of basal medium resides below the height of the basal medium compartment access port, the medium compartment access port can merely be an open port. However, if it is desirable for basal medium to reside at a height that is greater than the basal medium compartment access port, a seal is needed to prevent basal medium from spilling into the cell culture compartment. FIGS. 5A and 5B show one example of how to configure a basal medium access port cover that can act to retain basal medium in the basal medium compartment. The ability to use pipettes for liquid handling can be advantageous when it is desired to retain the simplicity of traditional devices such as flasks and roller bottles. The configuration shown in FIGS. 5A and 5B is adapted to allow pipette access. In FIG. 5A, basal medium compartment access port cover 80 is driven open by pipette 65, coil spring 85 is forced from its original position, and basal medium 30 is introduced into basal medium compartment 15D. When the pipette 65 is removed, coil spring 85 drives basal medium pipette access port cover 80 back into the sealing position. This allows the basal medium compartment to be entirely filled with medium, and to retain medium 30 when compartmentalized device 10A is laid on its side as shown in FIG. 5B.

When the basal medium compartment is configured with a basal medium access port cover, pressure can build up in the basal medium compartment during shipping or during use. In shipping, gas expands due to temperature changes and elevation changes commonly experienced in ground or air transport. In use, medium can off gas due to temperature changes, and the increased gas volume can pressurize the basal medium compartment. If the type of semi-permeable membrane that is integrated into the basal medium compartment does not have enough compliance, a pressure increase can damage the basal medium compartment integrity. Those skilled in the art will recognize that there are many ways of venting the basal medium compartment as pressure rises. For example, an umbrella check valve or poppet valve can be integrated into the basal medium compartment.

Figure 6:
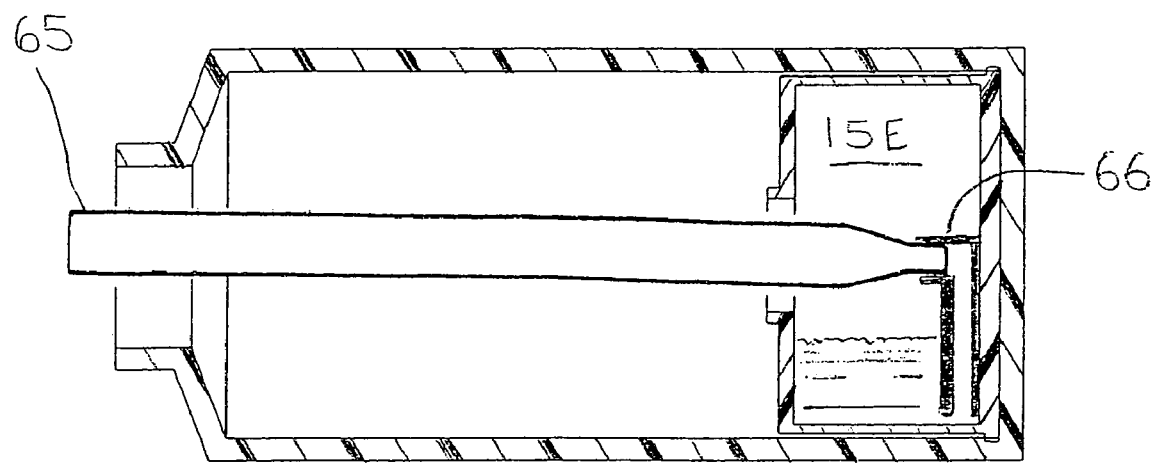
FIG. 6 shows one configuration for pipette collection of basal medium from the basal medium compartment when the compartmentalized device is in the horizontal position.

When a pipette is used to remove medium from the basal medium compartment, orienting the compartmentalized device at an angle that is closer to horizontal than vertical will make it more convenient to handle in a flow hood. One method of accessing the low point of the basal medium compartment, when the compartmentalized device is oriented at an angle that is closer to horizontal than vertical, is to create a conduit within the basal medium compartment. FIG. 6 shows a cross-section of an embodiment that achieves this objective. Pipette 65 is engaged into pipette interface 66, which creates a fluid flow path from the lower portion of basal medium compartment 15E to pipette 65. Pipette interface 66 should be constructed such that it creates a seal with pipette 65, but preferably releases pipette 65 easily so that pipette 65 does not detach from its vacuum pump. Co-pending U.S. application Ser. Nos. 10/460,850 and 60/517,288 incorporated herein in their entirety, are sources of information that provides guidance regarding this feature.

Figure 7A:
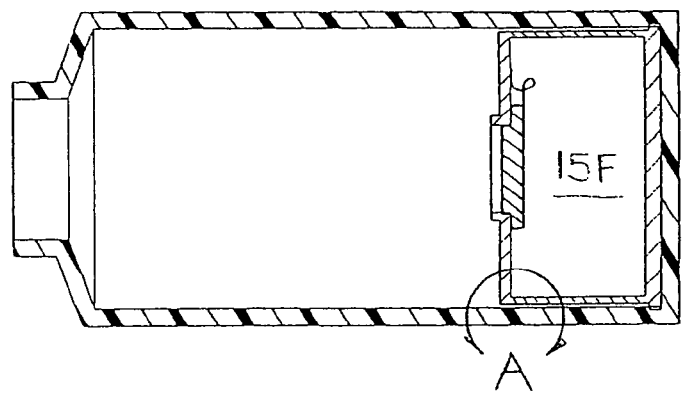
Figure 7C:
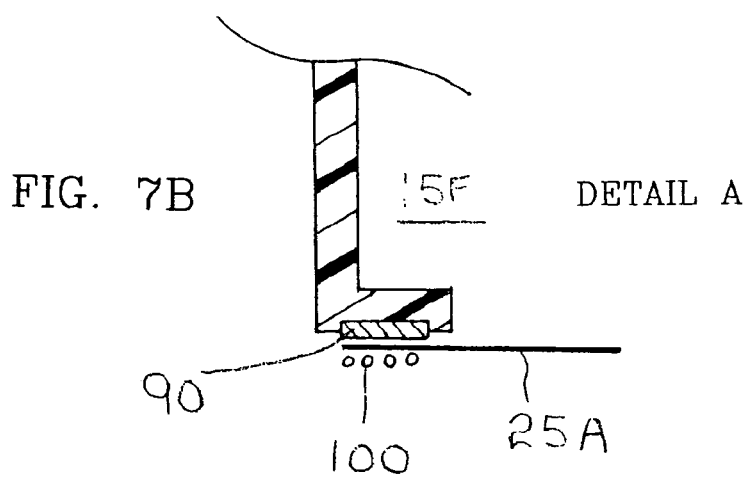
FIG. 7C shows one configuration for mating a semi-permeable membrane sheet to the basal medium compartment in a liquid tight manner.
Figure 7C:
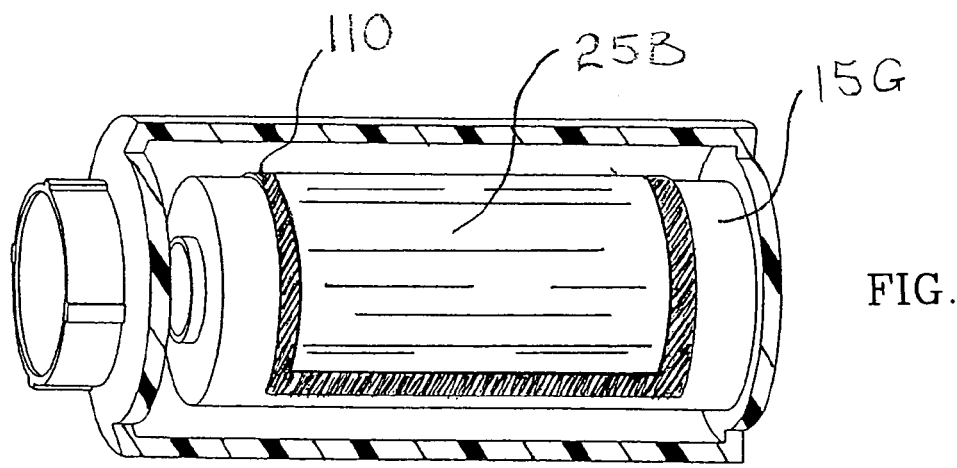

The semi-permeable membrane should be secured to the basal medium compartment in a liquid tight manner. FIGS. 7A and 7B show one configuration of attaching semi-permeable membrane 25A to basal medium compartment 15F when semi-permeable membrane 25A is extruded. FIG. 7B is a magnified view of detail A of FIG. 7A. Gaskets 90 mate to the housing of basal medium compartment 15F, and semi-permeable membrane 25A is placed over gaskets 90, and secured in a liquid tight manner to gaskets 90 by retaining wire 100. FIG. 7C shows a sheet semi-permeable membrane 25B secured to basal medium compartment 15G by adhesive 110. Those skilled in the art will recognize that many methods of securing the semi-permeable membrane to the basal medium compartment are possible, including mechanical squeeze, adhesives, potting compounds, sonic welds, and the like.

Figure 8A:
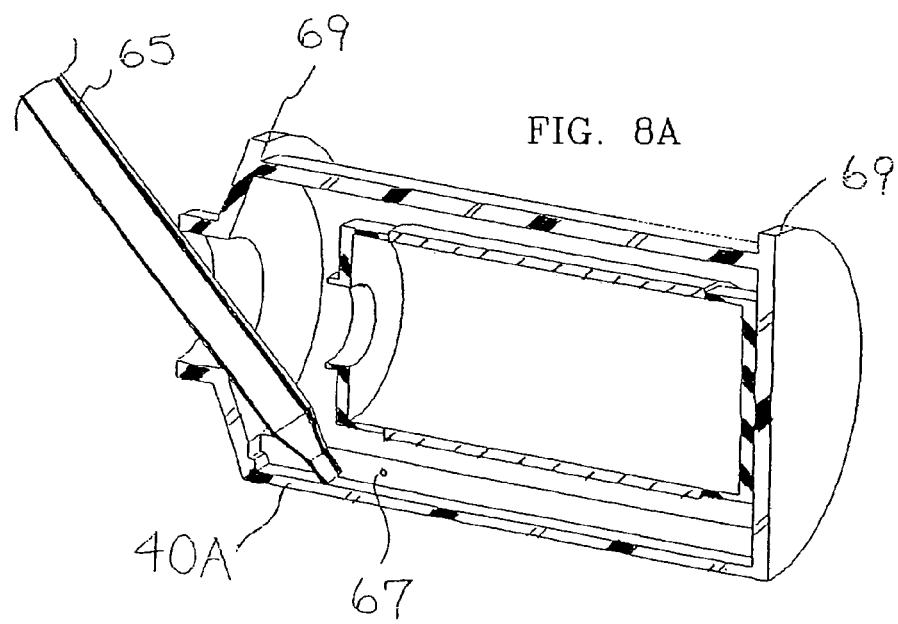
FIGS. 8A and 8B show various configurations for collecting liquid from the cell culture compartment.
Figure 8B:
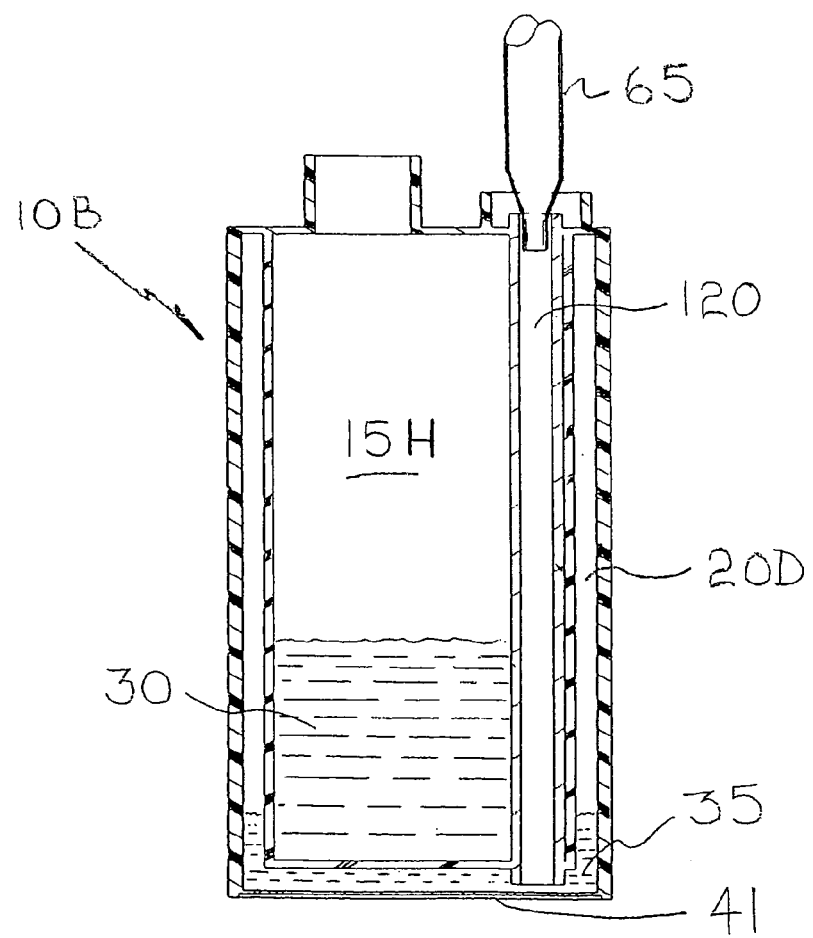

Collecting liquid from the cell culture compartment can be achieved in a variety of ways. FIG. 8A shows a very simple method in which pipette 65 is positioned in a manner such that the tip makes contact with groove 67 running the length of device housing 40A. Groove 67 provides a location for cell culture medium to collect in, and the tip of pipette 65 to be positioned in. Rims 69 ensure that the bottle is capable of rolling smoothly. FIG. 8B shows another method of collecting cell culture medium 35. Compartmentalized device 10B is oriented vertically. The tip of pipette 65 is docked into conduit 120, which travels through basal medium compartment 15H and into cell culture compartment 20D. Conduit 120 passes through basal medium compartment 15H in a liquid tight manner to prevent loss of basal medium 30. Basal medium compartment 15H is located a predetermined distance from device housing wall 41 so that cell culture medium 35 can collect at the distal end of conduit 120. In this manner, a vacuum applied to pipette 65 draws cell culture medium 35 through conduit 120 and into pipette 65. The tip of conduit 120 should seal against pipette 65, but not exert more force than would cause pipette 65 to get stuck in conduit 120 when attempting to withdraw pipette 65. Co-pending U.S. application Ser. Nos. 10/460,850 and 60/517,288 are sources of information that provides guidance regarding this feature.

In the case where the compartmentalized device is not a closed system, access port(s) into the basal medium compartment and/or the cell culture compartment can be covered by a cap that has the same function as that of a traditional roller bottle. In the loosened position, it allows gas exchange and prevents contamination. In the closed position, it can trap gas, such as is the case when 5% $CO_2$ environment resides within the cell culture compartment, but the compartmentalized device is operated in a warm room. If the compartmentalized device is structured as a closed system, it can either be periodically sparged with gas to provide oxygen and pH control, or at least a portion of device housing can be gas permeable so that gas exchange is adequate to maintain the culture. Co-pending U.S. application Ser. No. 10/961,814 provides a good reference for gas permeable device housings.

For adherent cell culture, the surface area within the compartmentalized device for cells to attach to can be increased by any methods known to those skilled in the art. Sources for guidance include those described in U.S. Pat. Nos. 3,941,661, 4,317,886, 4,824,787, 4,829,004, 4,912,058, or 6,130,080.

Figure 9A:
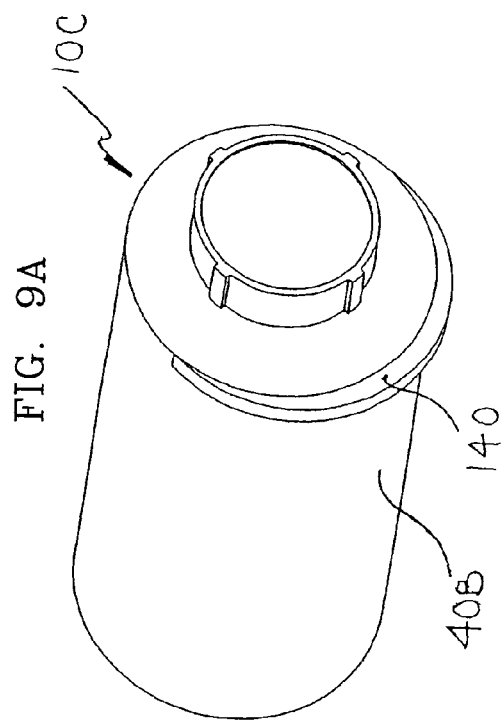
FIGS. 9A, 9B, and 9C show a configuration that rocks the compartmentalized device in an up and down motion as the compartmentalized device rolls.
Figure 9C:
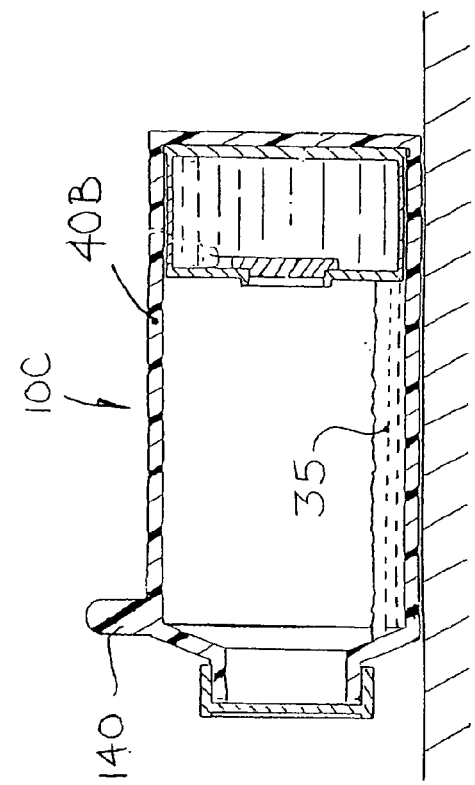
Figure 9B:
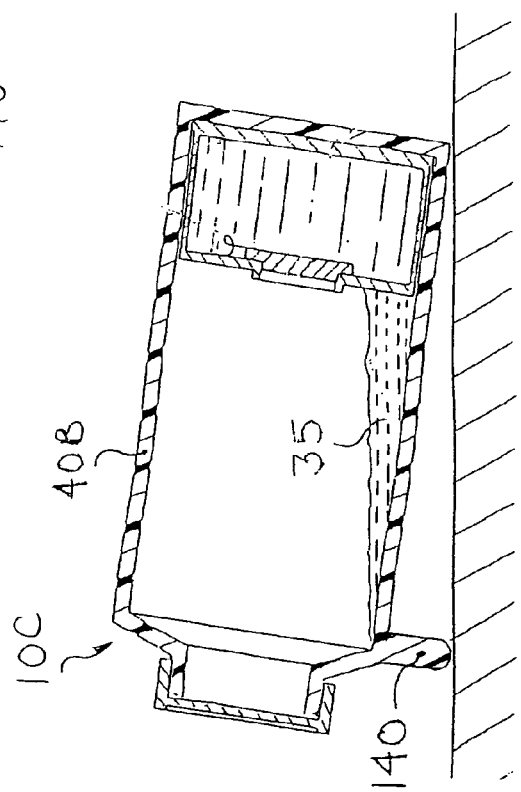

In the event that additional mixing of the cell culture medium is desired, such as may be the case when the volume of cell culture medium is very small, the location of the semi-permeable membrane is distant from portions of the cell culture medium, and/or for any other reason, that can be achieved. FIG. 9A shows a configuration that rocks the compartmentalized bottle in an up and down motion as the compartmentalized bottle rolls. FIGS. 9B and 9C show cross-sectional views of FIG. 9A at different time points. Eccentric 140 is positioned in proximity of one end of device housing 40B. As shown in FIGS. 9B and 9C, when compartmentalized bottle 10C rotates, eccentric 140 acts to lift and lower the end of device housing 40B. In this manner, cell culture medium 35 is repeatedly rocked back and forth, thereby breaking up any concentration gradients that may form. If desired, a second eccentric can be attached to the opposing end of the device housing to provide more vigorous rocking action. Other shapes beside eccentric can be utilized, such as a simple projection emanating at a point location. The device housing will be elevated as the projection passes the rollers of the roller rack. More than one projection, and/or projections on each end of the bottle, can be used to make the rocking action more vigorous.

Figure 10:
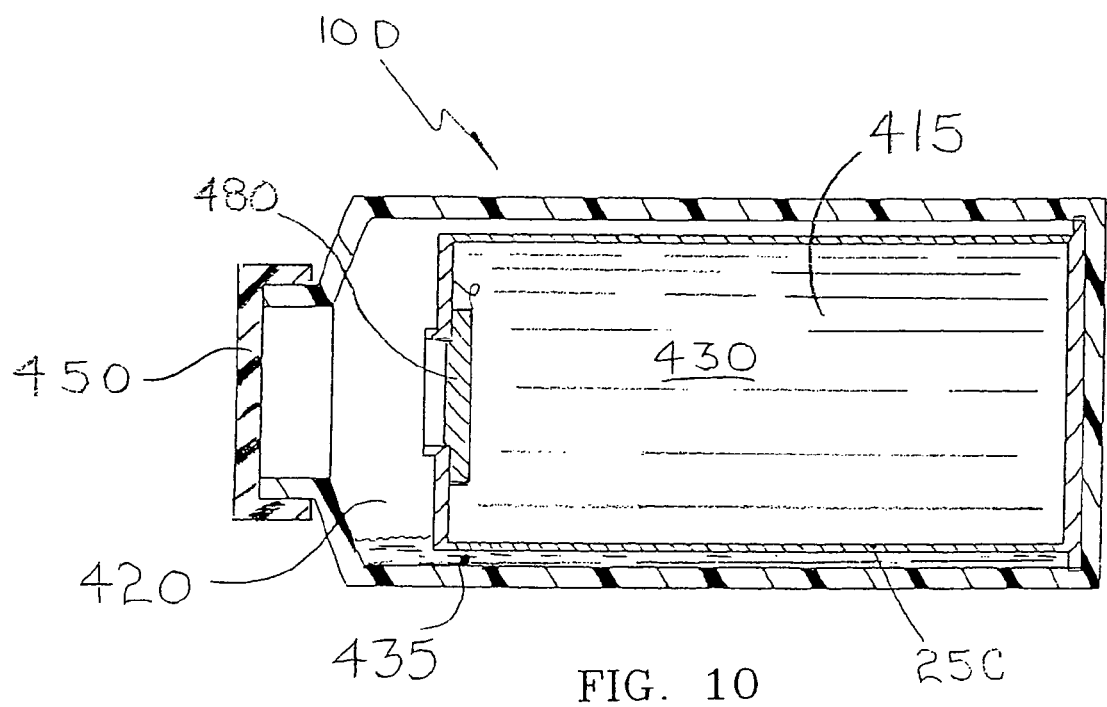
FIG. 10 shows a cross sectional view of a compartmentalized device that is advantageous for dialysis of laboratory samples.

The compartmentalized device can also be used to provide a more efficient device for dialysis of laboratory samples. FIG. 10 shows one embodiment of compartmentalized device 10D configured to achieve this objective. A dialysate compartment 415 is formed in any of the manners previously described for forming a basal medium compartment. A sample compartment 420 is formed in any of the manners previously described for forming a cell culture compartment. In the preferred embodiment, the MWCO of semi-permeable membrane 25C will be less than 100,000 Daltons, and often from 3,000 Daltons to 30,000, dialysate compartment 415 will have a dialysate compartment access port cover 480 configured as previously described for that of the basal medium access port cover, compartmentalized device 10D will be configured to roll in a roller rack, and cap 450 will be present to prevent accidental spilling or contamination of sample 435. In use, dialysate 430 is placed into dialysate compartment 415, and sample 435 is placed into sample compartment 420. Compartmentalized device 10D is rolled in a roller rack at any speed desired. Additional mixing can be attained using the techniques described previously in FIG. 9A through FIG. 9C. Periodically, dialysate can be removed and replaced. The advantage of this embodiment compared to alternative methods and devices for dialysis of laboratory samples are numerous, and are best understood after reviewing the prior art of U.S. Pat. Nos. 5,324,428, 5,783,075, and 5,503,741. Larger sample volumes can be processed with a high ratio of membrane surface area to sample volume, a stir bar is not needed, there is no need to properly orient the device in a dialysate container, needles are not needed, liquid can easily be handled with standard laboratory tools like pipettes and aspirators, the mess associated with liquid dripping from the dialysis membranes as they are removed from dialysate containers is avoided, sterility of the sample is easily maintained, and even the dialysate can easily be kept sterile.

Figure 11A:
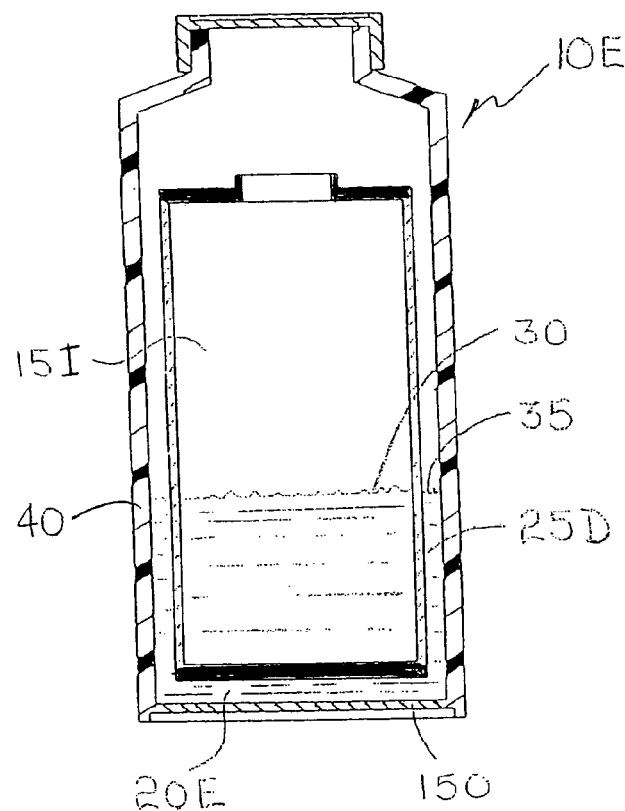
FIG. 11A shows a cutaway view of a compartmentalized device functioning without rolling.
Figure 11B:
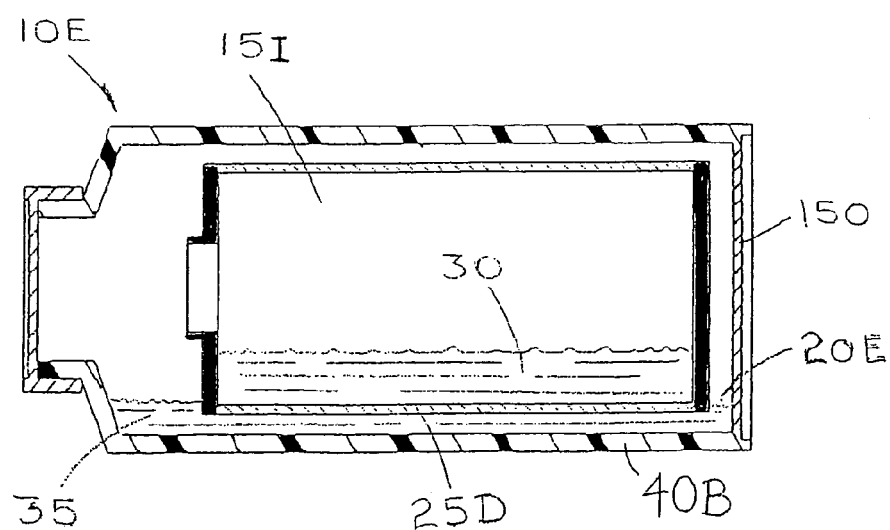
FIG. 11B shows a cutaway view of the compartmentalized device of FIG. 11A when rolling.

The compartmentalized device can be configured to function without rolling. For example, this may be advantageous when it is desired to reduce cell shear, or when rolling equipment is not available. FIG. 11A shows a cross-sectional view of compartmentalized device 10E configured in a manner that does not require rolling. Gas permeable bottom 150 allows gas exchange through the bottom of compartmentalized device 10E. The gas permeable material can be any material known to those skilled in the art of cell culture device design. Co-pending U.S. application Ser. No. 10/961,814, is among the many sources of information that can provide guidance. Basal medium compartment 151 resides a predetermined distance from gas permeable bottom 150. Cell culture compartment 20E contains cell culture medium 35 and basal medium compartment 151 contains basal medium 30. FIG. 11B shows how compartmentalized device 10E can function in the rolled position. Access to either compartment can be achieved as previously described.

When functioning in the unrolled position, cells come to reside in proximity of gas permeable bottom 150. Cell culture medium 35 is in communication with basal medium 30 by way of semi-permeable membrane 25D. Controlling the volume of cell culture medium 35 can be achieved by the distance that basal medium compartment 15I resides from gas permeable bottom 150 and from device housing 40. As the distance becomes smaller, for any given height of cell culture medium, the volume is reduced thereby increasing concentration. The ability to gain advantage by placing medium at heights beyond conventional wisdom is described in Co-pending U.S. application Ser. No. 10/961,814.

Another advantage of this configuration is the ability to balance hydrostatic pressure across the semi-permeable membrane. It is easy to construct a configuration with a high ratio of the volume of basal medium to the volume of cell culture medium, yet a small differential in height between the basal medium and the cell culture medium. Thus, the concentration advantages and feeding frequency advantages remain present, while the hydrostatic driving force across the semi-permeable membrane is reduced. As shown in FIG. 11A, the height of cell culture medium 35 and basal medium 30 are equal, balancing the hydrostatic pressure across semi-permeable membrane 25D. The difference in volume can be readily understood by calculating one of many possible geometric relationships. For example, basal medium volume would be 1100 ml and the volume of cell culture medium would be 295 ml if the compartmentalized device is cylindrical, basal medium compartment 15I resides 10 mm from device housing 40C per side, 10 mm from the gas permeable bottom 150, cell culture medium is place at a height of 15 mm, and the device housing has a diameter of 11 cm. Thus, the ratio of basal medium to cell culture medium would be about 3.7, showing that cells and cell secreted protein could be increased, perhaps by more than about 3.7 times depending on the feeding schedule. Co-pending U.S. application Ser. No. 10/961,814, incorporated herein in its entirety, gives guidance regarding medium height and the effect upon cell growth and secreted products.

Figure 11C:
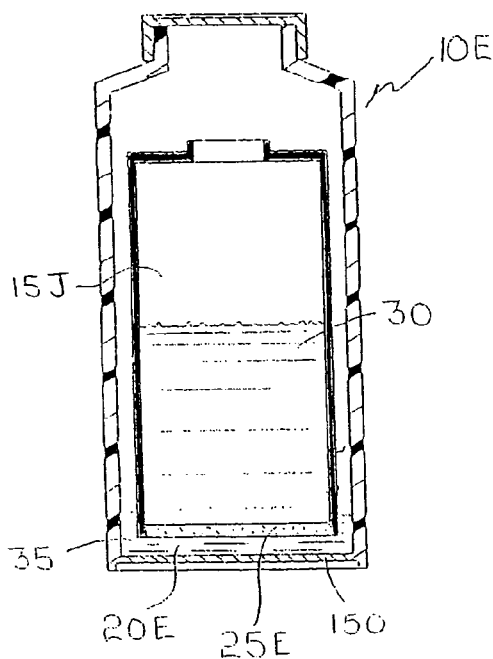
FIGS. 11C, 11D, and 11E show cutaway views of how the unrolled compartmentalized device can be structured to alter the ratio of semi-permeable membrane surface area to cell culture medium volume and control liquid flux across the semi-permeable membrane.
Figure 11D:
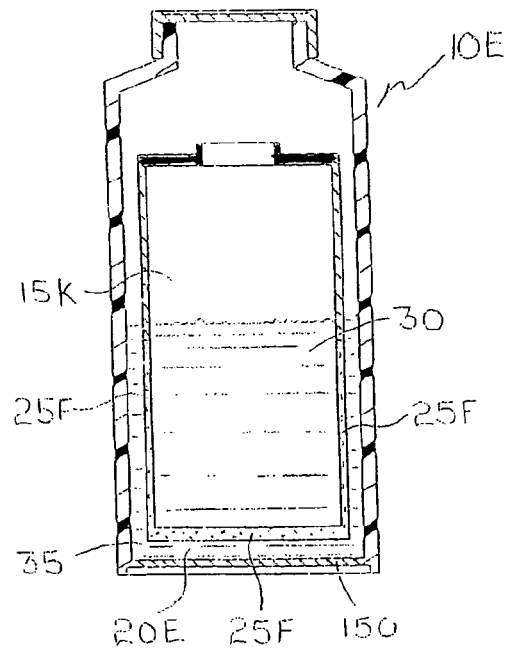
Figure 11E:
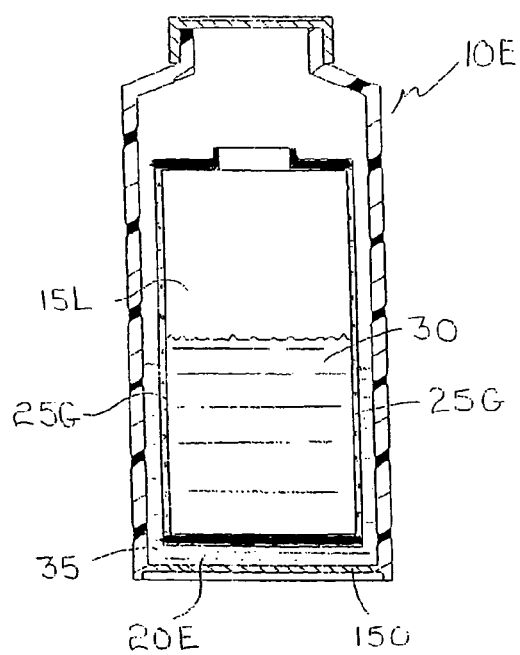

FIGS. 11C, 11D, and 11E show how the ratio of semi-permeable membrane area to basal medium volume can be changed to alter mass transfer or hydrostatically driven liquid flux. In FIG. 11C, the bottom of basal medium compartment 15J is comprised of semi-permeable membrane 25E, exposing basal medium 30 to mass transfer at the lower portion of basal medium 30. In FIG. 11D, the bottom and sides of basal medium compartment 15K are comprised of semi-permeable membrane 25F, exposing basal medium 30 to mass transfer at its bottom and sides, thereby increasing the surface area available for mass transfer. In FIG. 11E, the sides of medium compartment 15L are comprised of semi-permeable membrane 25G, exposing basal medium 30 to mass transfer at its sides.

Depending on the type of material used for the semi-permeable membrane and whether or not the compartmentalized device is rolled, structural support about the exterior of the semi-permeable membrane may be desired. For example, if the semi-permeable membrane bulges and firmly presses against the device housing, cell culture medium may be physically blocked or impeded from moving to about the perimeter of the semi-permeable membrane. Keeping the semi-permeable membrane from making detrimental physical contact with the device housing can be achieved in any number of ways including the use of an open weave mesh. If structural support is provided about the exterior of the semi-permeable membrane, the mesh or other physical structure should allow as much cell culture medium contact with the semi-permeable membrane as possible while allowing movement of the cell culture medium about the surface of the semi-permeable membrane. Prior to the use of structural support, mass transfer evaluation should be conducted to determine the effect of any given support configuration relative to no support. The rate of glucose transfer from the basal medium compartment into the cell culture compartment is one way of measuring the effect of the structural support upon mass transfer. In the case of hydrophilic membranes such as regenerated cellulose, transfer may be adequate without structural support.

Figure 12D:
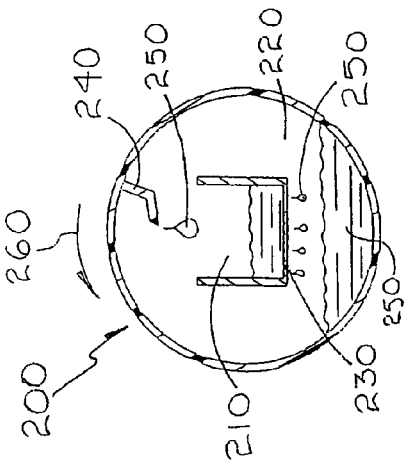
FIGS. 12B, 12C, and 12D show how the process occurs.
Figure 12A:
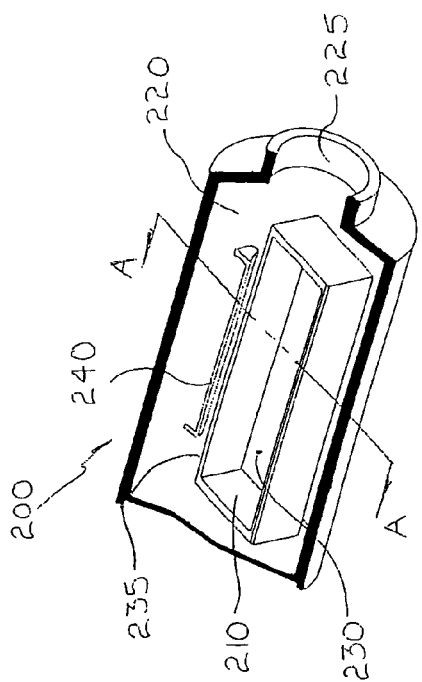
FIG. 12A shows a compartmentalized device capable of physically transporting fluid from one compartment to the other.
Figure 12C:
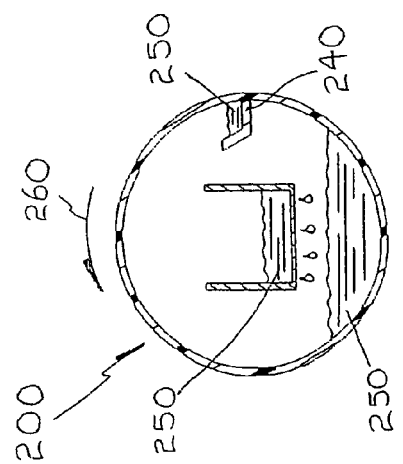
Figure 12B:
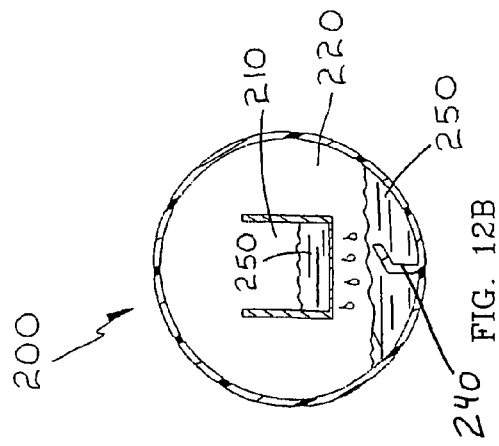

FIGS. 12A, 12B, 12C, and 12D show views of a compartmentalized device, configured to roll like a roller bottle, capable of physically transporting fluid from one compartment to the other. Compartmentalized device 200 contains suspended compartment 210, the bottom of which is comprised of semi-permeable membrane 230. Surrounding compartment 220 is bounded by device housing 235. Suspended compartment 210 mates to device housing 235 in a manner that allows it to remain in position as device housing rotates about it. Any number of mechanical attachment methods known to those skilled in the art are possible to allow that to occur, including the use of bearings, frictionless singe point attachment, rotary slip joints, and the like. When the cap is removed, access port 225 allows pipette access to each compartment. In operation, scoop 240 collects liquid from surrounding compartment 220 and delivers it to suspended compartment 210 as compartmentalized device 200 is rolled. FIGS. 12B, 12C and 12D, viewed from the perspective of section A-A of FIG. 12A, show the sequence of events that occur for liquid transport between surrounding compartment 220 and suspended compartment 210. In FIG. 12B, medium 250 resides in surrounding compartment 220 and suspended compartment 210. Scoop 240 is immersed in medium 250 residing in surrounding compartment 220. In FIG. 12C, compartmentalized device 200 has rotated in the counterclockwise direction as shown by rotation arrow 260. Scoop 240 has risen out of medium 250 and is filled with medium 250. In FIG. 12D, compartmentalized device 200 has rotated further in the counterclockwise direction as shown by rotation arrow 260. Scoop 240 is located above suspended compartment 210 and is oriented in a manner that allows medium 250 to exit by gravitational force. Medium 250 falls out of scoop 240 and enters suspended compartment 210. Medium 250 is also makes its way through semi-permeable membrane 230, and enters surrounding compartment 220. By balancing the volume of medium delivered by the scoop into the suspended compartment, with the amount of medium exiting the suspended compartment via semi-permeable membrane, a constant volume of medium is retained in each compartment while medium constantly moves from one compartment to the next. Altering the number of scoops used, the liquid capacity of the scoop, the rate of rotation, the permeability of the semi-permeable membrane, and the surface area of the semi-permeable membrane can strike that balance. In the preferred embodiment, device housing 235 is cylindrical so that smooth movement occurs during rotation and optically clear so that the fluid flow can be monitored.

This configuration can be very helpful for a variety of applications. A main attribute is the ability to move liquid from one compartment to the next on a continuous basis without the need for pumps. For example, if hematopoietic cells are to be transduced, moving vectors continuously past them creates a higher incidence of contact than simple Brownian motion. Hematopoietic cells can be placed in the suspended compartment, and the characteristics of the semi-permeable can be selected to retain the cells in the suspended compartment, but let medium and vectors pass. When vectors are introduced into the suspended compartment by the scoop, they make their way toward the surrounding compartment by gravity, contacting the hematopoietic cells. Vectors that do not transduce a hematopoietic cell, and pass to the surrounding compartment are then returned to the suspended compartment by the scoop and have another chance to transduce the cell. In this case it is important that the medium residing in the suspended compartment does not drain completely, which would cause the cells to die.

Other examples for which this configuration could be useful include the desire to perfuse each compartment with cell-secreted product, or any exogenous factors, or for co-culture. In this case, cells can be located in the suspended compartment and the surrounding compartment. Liquid surrounding the cells is constantly moved from the surrounding compartment to the suspended compartment, and back again.

Figure 13A:
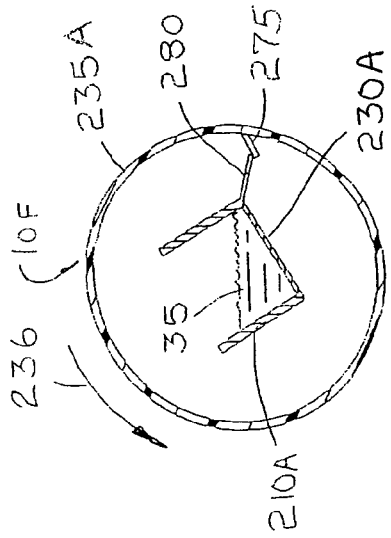
FIGS. 13A, 13B, 13C, and 13D show a compartmentalized device configured with a suspended compartment that can be moved to create liquid action similar to that of a shaker plate.
Figure 13B:
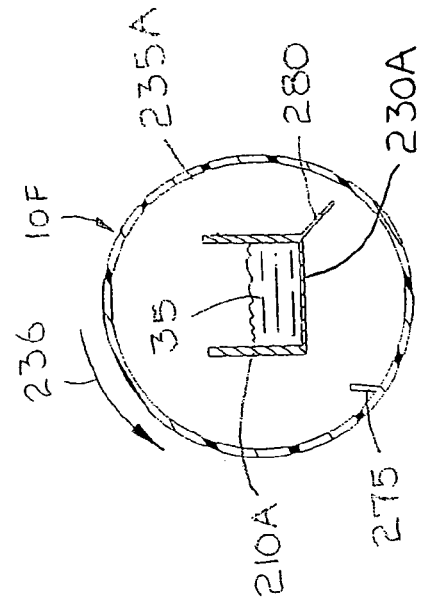
Figure 13C:
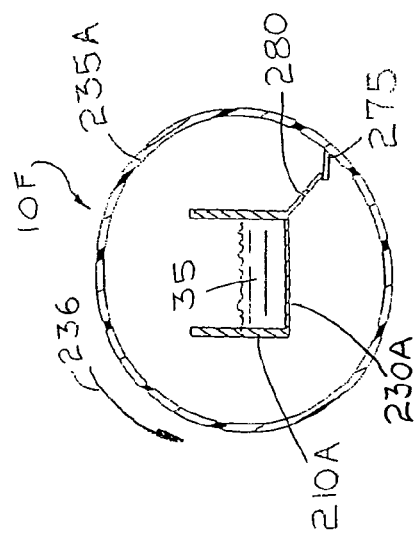
Figure 13D:
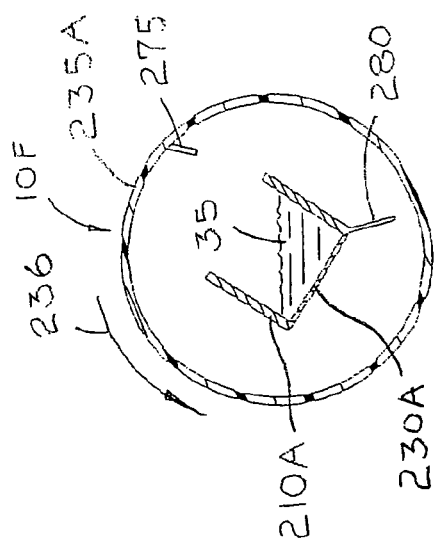

In many applications with traditional culture devices, they are placed upon shaker plates. When a compartmentalized device is configured with a suspended compartment that remains in position as the device housing rotates about it, it can create a similar action as a shaker plate. FIGS. 13A, 13B, 13C, and 13D show a cross-sectional view of such a compartmentalized device. FIG. 13A through FIG. 13D depict the motion that the suspended compartment and cell culture medium go through as the compartmentalized device rotates. Preferably, the compartmentalized device is configured to roll on a standard roller rack. Compartmentalized device 10F integrates suspended compartment 210A. FIG. 13A shows suspended compartment 210A at rest. As device housing 235A rotates about suspended compartment 210A, as shown by rotation direction arrow 236, device housing projection 275 makes contact with suspended compartment projection 280 and drives suspended compartment from its resting position, as best shown in FIG. 13B. The contact forces suspended compartment 210A to rotate about its pivot point contact with device housing 235A until device housing projection 275 loses contact with suspended compartment projection 280, at which point suspended compartment 210A swings back past its original position, as best shown in FIG. 13C. As gravity exerts is force on suspended compartment 210A, it comes to rest as best shown in FIG. 13D. The amount of agitation to cell culture medium 35 can be varied by the rate of rotation, the duration of contact between the device housing projection and suspended compartment projection, and the number of device housing projections.

In the case where culture of cells upon a gas permeable membrane is desired, the configuration shown in FIG. 13A through FIG. 13D can useful for periodically mixing cells. In that case, the selection of material for semi-permeable membrane 230A is based on the capacity to provide gas transfer to cells residing above it. U.S. Pat. No. 5,693,537 is among the many sources of information that provides guidance for the material selection of the gas permeable membrane. Co-pending U.S. application Ser. No. 10/961,814 describes the how to structure gas permeable devices for the culture of cells and provides guidance of specific design attributes that can be applied to the design of suspended compartment 210A to optimize culture performance.

EXAMPLES

Example 1

Figure 14:
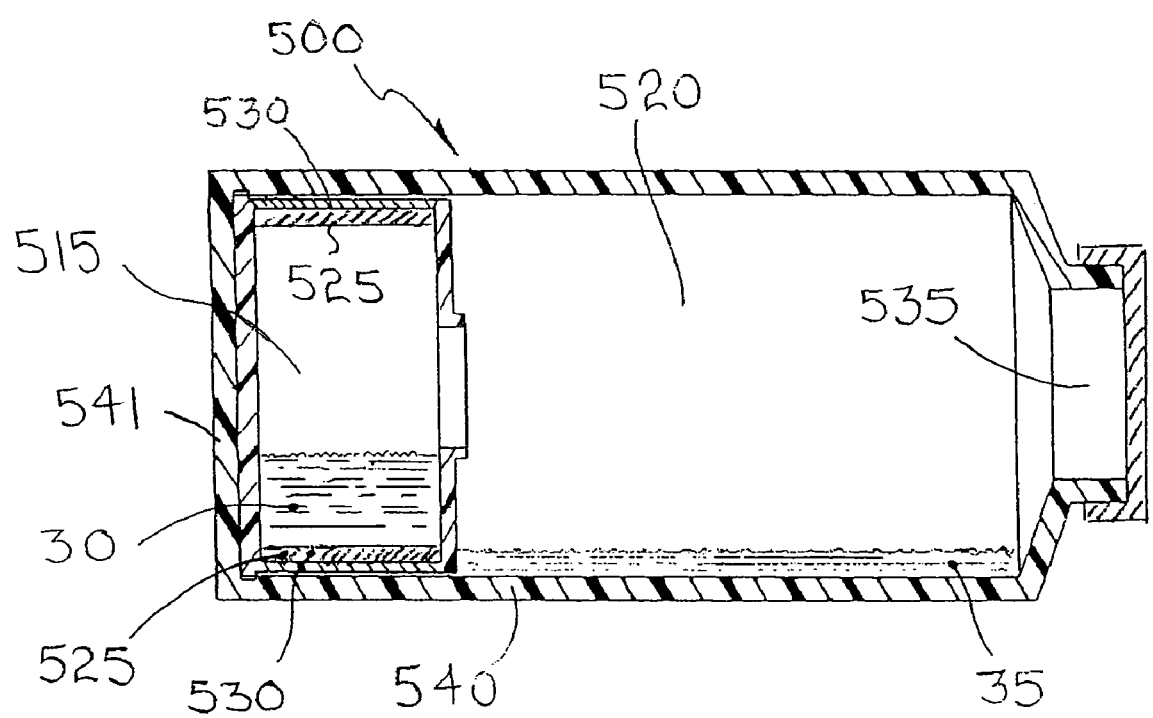
FIG. 14 shows a cross-section of a compartmentalized device used to generate data of Example 1, Example 2, and Example 3.

Evaluation of the Compartmentalized Device With Adherent Cells for Increased Cell Density and Reduction of Serum Use Compartmentalized device test fixtures 500 were configured as shown in FIG. 14. The device housing was created by modifying a Corning® 850 cm² roller bottle. The bottom of the bottle was removed to form device housing 540. Basal medium compartment 515 was placed in the distal end of device housing 540 as shown. Device bottom 541 was attached in a liquid tight manner, thereby completing the assembly procedure and creating a liquid tight cell culture compartment 520. Semi-permeable membrane 525 consisted of a 14,000 MWCO cellulose membrane 1.0 inch long and 4.4 inches in diameter, creating a semi-permeable membrane surface area of 89 cm¹. Semi-permeable membrane 525 was constrained from expanding by mesh 530, comprised of 0.020 inch diameter polypropylene strands at 16 strands per inch. The inside surface area of device housing 540 available for cell attachment was the surface that resided between basal medium compartment 515 and access port 535, which was approximately 490 cm².

Growth of an adherent CHO cell line, CHO-ACE005, was evaluated in six compartmentalized device test fixtures 500 relative to a traditional roller bottle. The capability to support the growth of cells at high density, and to reduce the use of serum was assessed. To assess growth of cells at high density in the compartmentalized devices, the medium volume to growth surface area ratio was reduced well below that of the traditional Corning® 490 cm² roller bottle controls. The traditional Corning® 490 cm² roller bottle controls contained 115 ml of medium, while each compartmentalized device test fixture 500 contained only 30 ml in cell culture compartment 520. Additional medium support, 85 ml, was provided by basal medium compartment 515. Thus, all test devices had 115 ml of total medium, but only 30 ml was in direct contact with cells in the compartmentalized device test fixtures 500 versus 115 ml in the traditional bottle.

Further benefits can be derived if the compartmentalized devices are capable of reducing the use of serum. To evaluate this potential benefit, all six compartmentalized device test fixtures 500 had 10% serum in cell culture compartment 520. Three compartmentalized device test fixtures 500 had 10% serum in basal medium compartment 515, and three compartmentalized device test fixtures 500 had no serum in the basal medium.

DMEM medium was used for all devices, supplemented with serum as described. All devices were rotated at 1 RPM at 37 C, 95% RH, and 5% $CO_2$.

Adherent cells were rinsed with PBS and collected by two rounds of trypsinization (0.25% Trypsin, 1 mM EDTA.4Na). Cells were stained with trypan blue to determine viability and enumerated using a hemocytometer. Cell density, identified as "cells per ml" in Table E1, was calculated per ml of cell culture medium. Thus, the total quantity of cells recovered from each compartmentalized device test fixture was divided by 30 ml, while the total quantity of cells recovered from each roller bottle control was divided by 115 ml. All values were averaged and Table E1 summarizes the findings.

TABLE E1

| Device | Serum used | Viability | Viable Cells Recovered | Cells per ml |
|---|---|---|---|---|
| Roller bottle control | 34.5 ml | 95% | $59.78 \times 10^6$ | $0.52 \times 10^6$ |
| Compartmentalized device with serum | 25.5 ml | 90% | $58.45 \times 10^6$ | $1.95 \times 10^6$ |
| Compartmentalized device w/o serum in basal medium compartment | 3 ml | 90% | $60.35 \times 10^6$ | $2.01 \times 10^6$ |

Table E1 clearly shows the capacity of the compartmentalized device to make cell culture more efficient. Despite over a 10-fold reduction in serum use, the number of viable cells cultured was not impeded. Furthermore, the concentration of cells in the medium was increased nearly 4-fold.

Example 2

Evaluation of the Compartmentalized Device with Suspension Cells for Increased Antibody Density and Reduction of Serum Use Four gamma-irradiated compartmentalized device test fixtures 500 were constructed as previously described in Example 1, and shown in FIG. 14. Tests were conducted to evaluate the ability of the compartmentalized device test fixtures to increase the density of secreted antibody, the amount of secreted antibody, and reduce serum relative to traditional roller bottles.

$22 \times 10^6$ murine hybridoma cells secreting IgG monoclonal antibody were suspended in 25 ml of medium and were inoculated into each cell culture compartment 520, and 75 ml of medium was placed into each basal medium compartment 515. $22 \times 10^6$ murine hybridoma cells secreting IgG monoclonal antibody were suspended in 100 ml of medium and were inoculated into traditional Corning® 490 cm² roller bottle controls. Glucose consumption was monitored daily. FBS serum concentration was 10% for the traditional Corning® 490 cm² roller bottle controls and for all medium in two compartmentalized device test fixtures 500. However, two compartmentalized device test fixtures 500 contained FBS serum at 10% concentration in cell culture compartment 520, with no FBS serum in basal medium compartment 515. All devices were rotated at 1 RPM in ambient conditions of 37 C, 95% RH, and 5% $CO_2$. Samples were collected from each cell culture compartment 520, and from the roller bottle controls every 5 days. ELISA was performed to determine antibody production. Results are shown in Tables E2.1 and E2.2.

operation expanded from swelling to make contact with device housing 540. Device housing 540 extended approximately seven inches between basal medium compartment 515 and access port 535, generating a device housing surface area suitable for cell culture of approximately 600 cm².

Two compartmentalized test devices and a T-175 control flask were compared on the basis of cell density. Medium consisted of Hyclone media (cat#SH30382.02) supplemented with 10% Hyclone Fetal Bovine Serum and 1% Gibco Penicillin Streptomycin. Culture conditions were 37 C, 95% R.H., and 5% $CO_2$. All devices were rolled at 1 RPM. Each cell culture compartment 520 was inoculated with 25×10⁶ murine hybridoma cells in 25 mls of medium. Each basal medium compartment 515 received 170 ml of medium. A T-175 control flask was inoculated with 25×10⁶/ml murine hybridoma cells in 25 ml of the same medium.

TABLE E2.1

Monoclonal antibody concentration in compartmentalized device test fixtures compared to the roller bottle control.

| Device (n = 2) | FBS Serum Concentration | IgG concentration (μg/mL, mean +/− sd) | | | |
|---|---|---|---|---|---|
| | | Day 5 | Day 10 | Day 15 | Day 20 |
| Compartmentalized device | 10% in both compartments | 202 +/− 23 | 320 +/− 42 | 1,695 +/− 192 | 1,301 +/− 464 |
| Compartmentalized device | 10% in basal medium compartment 0% in cell culture compartment | 197 +/− 87 | 282 +/− 4 | 1,593 +/− 533 | 1,187 +/− 578 |
| Roller Bottle Control | 10% | 35 +/− 6 | 36 +/− 5 | 71 +/− 2 | 71 +/− 2 |

Table E2.1 demonstrates that each compartmentalized device test fixture 500 generated at least a 16-fold increase IgG monoclonal antibody concentration relative to the traditional roller bottle controls.

TABLE E2.2

Monoclonal antibody produced

| Device, n = 2 | Total IgG produced μg/ml (mean +/− sd) | FBS added ml (mean +/− sd) | Medium added ml (mean +/− sd) | Glucose consumed per mg IgG (mean +/− sd) |
|---|---|---|---|---|
| Compartmentalized Device | 51,933 +/− 641 | 6 +/− 1 | 806 +/− 50 | 0.0282 +/− 0.0015 |
| Compartmentalized Device | 58,565 +/− 8,202 | 82 +/− 6 | 731 +/− 45 | 0.0272 +/− 0.0032 |
| Traditional | 34,098 +/− 268 | 78 +/− 1 | 703 +/− 1 | 0.0387 +/− 0.0019 |

Table E2.2 demonstrates that total amount of antibody produced in compartmentalized device test fixtures 500 (n=4) increased at least 52% compared to the traditional roller bottle controls (n=2, p<0.001 by unpaired t-test analysis). Also of importance, a 13-fold reduction in FBS serum use had no effect on the total amount of IgG produced (p<0.05). Furthermore, there quantity of glucose used per mg of antibody produced was reduced by at least 28%, suggesting a more efficient use of medium. In summary, the ability of the compartmentalized device to increase production, concentrate product can lead to substantial cost reductions in downstream processing. Furthermore, reduced use of expensive serum can cost reduce the culture process. Thus, the compartmentalized device is far superior to the traditional roller bottle.

Example 3

Evaluation of the Compartmentalized Device With Suspension Cells for Increased Cell Density Compartmentalized test devices were configured as shown in FIG. 14 with the exception that mesh 530 was not present. Semi-permeable membrane 525, was unconstrained, and in All test devices were fed as needed to keep the cells viable. Table E3 shows maximum viable cells density, and maximum viable cells attained in each device.

TABLE E3

| TEST DEVICE | Max cell density (×10⁶/ml) | Max total cells (×10⁶) |
|---|---|---|
| 1ˢᵗ Compartmentalized Test Device | 22 | 548 |
| 2ⁿᵈ Compartmentalized Test Device | 21 | 520 |
| T-175 Flask | 3.6 | 90 |

The power of the compartmentalized device to increase cell density relative to the commonly used tissue culture flask was demonstrated. Cell density increased at least approximately 600%.

Example 4

Evaluation of Unrolled Compartmentalized Devices With Suspension Cells for Increased Cell and Cell Secreted Protein Density Tests were conducted to evaluate the capacity of the compartmentalized device to function in the unrolled state. Three configurations of unrolled compartmentalized devices were created, each with a different semi-permeable membrane surface area. These configurations were evaluated relative to the traditional T-175 flask. In a murine hybridoma application to obtain monoclonal antibody, a comparison was made with respect to cell density.

Figure 15B:
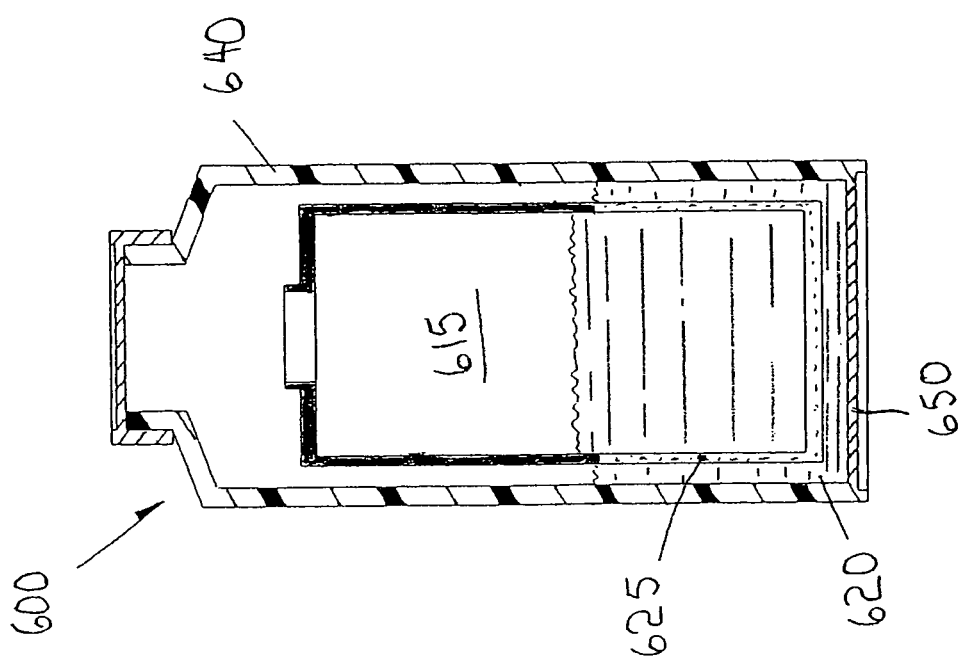
FIGS. 15A and 15B show compartmentalized devices of Example 4, configured to culture cells in the unrolled position.
Figure 15A:
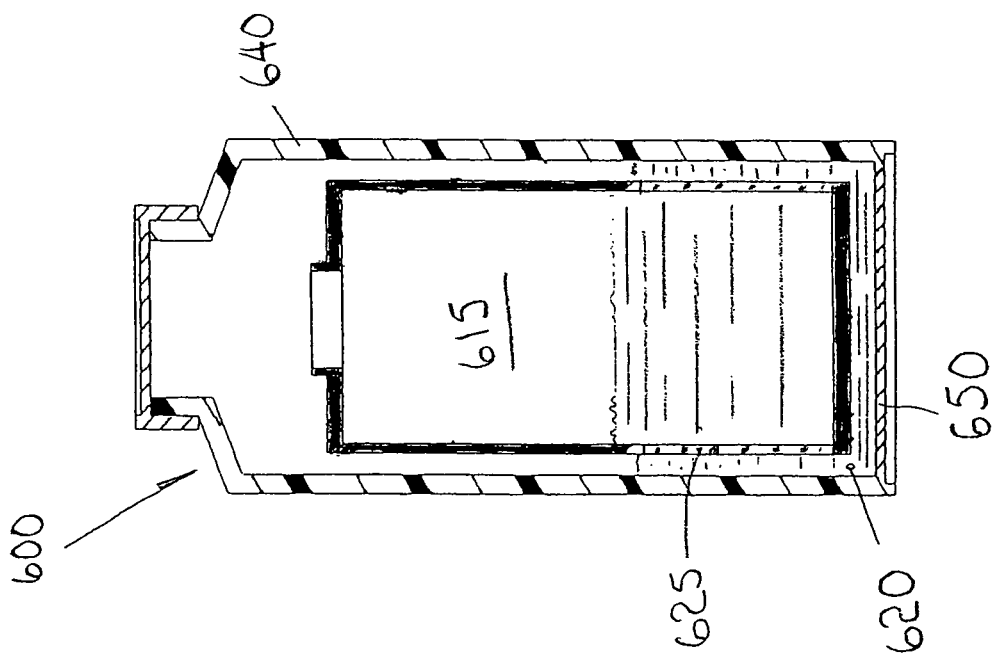

Two styles of compartmentalized test devices were configured in a similar manner as that described in FIGS. 11E and 11D, further defined as shown in FIGS. 15A and 15B respectively. The compartmentalized test devices are hereinafter identified as Test Device 600A and Test Device 600B respectively. Test Device 600A and Test Device 600B differed in the amount of semi-permeable surface area in contact with cell culture medium. For each test device, the device housing was created by modifying a Corning® 850 cm$^2$ roller bottle. The bottom of the bottle was removed to form device housing 640. Basal medium compartment 615 was placed in the location shown. Gas permeable device bottom 650, comprised of 0.004 inch thick di-methyl silicone of 98 cm$^2$, was attached to device housing 640 in a liquid tight manner, thereby creating a liquid tight cell culture compartment 620. Semi-permeable membrane 625 in each device consisted of 14,000 MWCO cellulose membrane. Test Device 600A, as shown in FIG. 15A, had semi-permeable membrane 625 comprising the perimeter of cylindrical basal medium compartment 615, extending a height of 1.0 inch from the bottom of basal medium compartment 615. Test Device 15B, as shown in FIG. 15B, had semi-permeable membrane 625 comprising the perimeter of cylindrical basal medium compartment 615, extending a height of 1.0 inch from the bottom of basal medium compartment 615, and comprising the bottom of basal medium compartment 615. Table E4 summarizes the two styles of compartmentalized test devices and the control T-175 flask.

Murine hybridoma cells were cultured in Hyclone medium. Cell counts and viability were monitored made using standard hemocytometer and trypan blue exclusion methods. Each compartmentalized device was inoculated on "Day 0" with murine hybridoma cells. Table E4.1 shows the results.

TABLE E.4.1

| Test Device | Semi-permeable membrane surface area in contact with cell culture medium (cm$^2$) | Day 0 inoculation density (×10$^6$/ml) | Maximum live cell density (×10$^6$/ml) |
|---|---|---|---|
| 600A | 81 | 3.74 | 9.12 |
| 600B | 152 | 3.74 | 14.28 |
| T-175 standard control | NA | 1.0 | 3.92 |

These results clearly indicate the ability of the unrolled compartmentalized device to culture cells a much higher density than traditional culture devices such as the tissue culture flask. Importantly, increasing semi-permeable membrane surface area can yield additional culture capacity without increasing the footprint of the device. This allows more efficient use of space.

Those skilled in the art will recognize that numerous modifications can be made thereof without departing from the spirit. Therefore, it is not intended to limit the breadth of the invention to the embodiments illustrated and described. Rather, the scope of the invention is to be interpreted by the appended claims and their equivalents. Each publication, patent, patent application, and reference cited herein is hereby incorporated herein by reference.

The invention claimed is:

1. A compartmentalized roller bottle device comprising:
   a device housing having a longitudinal axis, at least a portion of said device housing including structural means to roll on a roller rack;
   a basal medium compartment having a longitudinal axis residing within said device housing, said basal medium compartment having a sidewall of which at least a portion is comprised of a semi-permeable, non-microporous membrane;
   said basal medium compartment including a rigid structure for maintaining the longitudinal axis of said basal medium compartment in the same direction as said longitudinal axis of said device housing when liquid resides within said basal medium compartment;
   the space within said device housing that is not occupied by said basal medium compartment forming a cell culture compartment;
   a first access port providing fluid access to said basal medium compartment;
   a second access port providing fluid access to said cell culture compartment, and a means of providing gas exchange between said cell culture compartment and ambient gas other than by requiring gas to only enter said cell culture compartment by traversing said semi-permeable membrane of said basal medium compartment.

2. The device of claim 1 wherein said semi-permeable membrane is capable of preventing passage of substances greater than or equal to 0.1 microns.

3. The device of claim 1 wherein said semi-permeable membrane is capable of preventing passage of substances greater than or equal to 0.01 microns.

4. The device of claim 1 wherein said basal medium compartment is generally cylindrical.

5. The device of claim 1 wherein said sidewall of said basal medium compartment sidewall includes a first section oriented a first distance from said outer housing sidewall and a second section oriented a second distance from said outer housing sidewall, wherein either said first section or said second section is not in contact with the device housing.

6. The device of claim 1 wherein said basal medium compartment includes means for rotating in the same direction of said device housing when said device housing is rolling in the horizontal position.

7. The device of claim 1 wherein said basal medium compartment includes means for rotating in the opposite direction of said device housing when said device housing is rolling in the horizontal position.

8. The device of claim 1 wherein said basal medium compartment includes a basal medium access port cover.

9. The device of claim 1 wherein said basal medium compartment includes a vent.

10. The device of claim 1 wherein the wall of said cell culture compartment includes a groove for the collection of cell culture medium.

11. The device of claim 1 including at least one projection that emanates from the outside of said device housing in order to create a rocking motion when said device housing is rolling in the horizontal position for the purpose of mixing cell culture medium.

12. The device of claim 1 including means for preventing said semi-permeable membrane from making contact with said device housing in order to enhance cell culture medium communication with said semi-permeable membrane.

13. The device of claim 1 wherein said device housing is comprised at least in part of a gas permeable material.

14. The apparatus of claim 1 in which said non-microporous membrane includes cellulose.

15. The apparatus of claim 1 in which said non-microporous membrane substantially prevents medium from moving across it when about a 3 $cm^2$ surface area of said non-microporous membrane resides below medium at a head height of about 2 inches.

16. A method of culturing cells in the device of claim 1 including:
   adding cells and a volume of cell culture medium to said cell culture compartment;
   adding a volume of basal medium to said basal medium compartment;
   placing the compartmentalized roller bottle device on a roller rack.

17. The method of claim 16 wherein said volume of basal medium exceeds said volume of said cell culture medium.

* * * * *